(12) United States Patent
Yeh et al.

(10) Patent No.: US 6,720,331 B2
(45) Date of Patent: Apr. 13, 2004

(54) 1-SUBSTITUTED 1,2,3,4-TETRAHYDRO-β-CARBOLINE AND 3,4-DIHYDRO-β-CARBOLINE AND ANALOGS AS ANTITUMOR AGENTS

(75) Inventors: Sheau Farn Yeh, Taipei (TW); Ya-Ching Shen, Kaohsiung (TW)

(73) Assignees: National Sun Yat-sen University, Kaohsiung (TW); National Yang-Ming University, Taipei (TW)

( * ) Notice: Subject to any disclaimer, the term of this patent is extended or adjusted under 35 U.S.C. 154(b) by 0 days.

(21) Appl. No.: 10/115,312

(22) Filed: Apr. 3, 2002

(65) Prior Publication Data

US 2003/0040527 A1 Feb. 27, 2003

Related U.S. Application Data

(60) Provisional application No. 60/281,531, filed on Apr. 3, 2001.

(51) Int. Cl.[7] .................. A61K 31/437; C07D 471/04; A61P 35/00
(52) U.S. Cl. .................. 514/292; 546/85; 546/86; 546/87
(58) Field of Search .................. 514/292; 546/85, 546/86, 87

(56) References Cited

U.S. PATENT DOCUMENTS 6,069,150 A  5/2000  Spinelli et al.

OTHER PUBLICATIONS

Y. Shen et al., "Bioactive Constituents from Haliclona sp., a Formosan Marine Sponge," The Chinese Pharmaceutical Journal, 1996, 48, pp. 1–10.
J. Allen et al., "The Simple β–Carboline Alkaloids," Phytochemistry, 1980, vol. 19, pp. 1573–1582.
G. Pimpinella et al., "Interaction of β–carbolines with central dopaminergic transmission in mice: structure–activity relationships," Neuroscience Letters 189 (1995), pp. 121–124.
B. Wiczynska et al., "Antidepressant profile of 9–methyl–2 [–3–(4–phenyl–1–piperazinylpropyl)]–1,2,3, 4–tetrahydro–beta–carbolin–1–one (B–193)," Pol J. Pharmacol Pharm Jul.–Aug. 1989; 41(4):331–44; 1 page.
G. Dorey et al., "Synthetic Routes to 4–Amino–3–carboxy–β–carboline Derivatives: Incidental Formation of Novel Furo[3,4–c]–β–carbolin–2–ones Displaying High Affinities for the Benzodiazepine Receptor," J. Med. Chem. 1995, 38, pp. 189–198.
L. Larsen et al., "β–Carbolines from the Blue–Green Alga Dichothrix Baueriana," Journal of Natural Products, vol. 57, No. 3, pp. 419–421, Mar. 1994.

T. Kurihara et al., "Meisenheimer Rearrangement of Azetopyridoindoles. VIII.[1)] Synthesis and Antiviral Activities of 12–Carbaeudistomin Analogs," Chem. Pharm. Bull. 44(5) pp. 900–908 (1996).
S. Adesanya et al., "Brominated β–Carbolines from the Marine Tunicate Eudistoma Album," Journal of Natural Products, vol. 55, No. 4, pp. 525–527, Apr. 1992.
B. Lee et al., "Suppression of inducible nitric oxide synthase expression in RAW 264.7 macrophages by two β–carboline alkaloids extracted from Melia azedarach," European Journal of Pharmacology 406 (2000) pp. 301–309.
K. Narasimha Rao et al.; "Thymidylate Synthase Activity and the Cell Growth Are Inhibited by the β–Carboline–Benzoquinolizidine Alkaloid Deoxytubulosine," J. Biochem Molecular Toxicology, vol. 12, No. 3, 1998, pp. 167–173.
J. Osiadacz et al., "Sequence–Selectivity of 5,11–Dimethyl–5H–indolo[2,3–b]quinoline Binding to DNA. Footprinting and Molecular Modeling Studies," Bioorganic & Medicinal Chemistry 8 (2000), pp. 937–943.
S. Mahboobi et al., "beta–Carbolinedione derivatives as topoisomerase I inhibitors," Arch Pharm (Weinheim) Jul. 1999; 332(7):249–54; 1 page.
F. Pognan et al., "A Carboline Derivative as a Novel Mammalian DNA Topoisomerase II Targeting Agent," Biochemical Pharmacology, vol. 44, No. 11, pp. 2149–2155, 1992.
P. Fossé et al., "Stimulation by γ–Carboline Derivatives (Simplified Analogues of Antitumor Ellipticines) of Site Specific DNA Cleavage by Calf DNA Topoisomerase II," Biochemical Pharmacology, vol. 39, No. 4, pp. 669–676, 1990.
W. Peczyńska–Czoch et al., "Synthesis and Structure—Activity Relationship of Methyl–Substituted Indolo[2,3–b] quinolines: Novel Cytotoxic, DNA Topoisomerase II Inhibitors," J. Med. Chem. 1994, 37, pp. 3503–3510.
Y. Funayama et al., "Effects of β– and γ–carboline derivatives on DNA topoisomerase activities," Mutation Research 349 (1996), pp. 183–191.
F. Denizot et al., "Rapid colorimetric assay for cell growth and survival: Modifications to the tetrazolium dye procedure giving improved sensitivity and reliability," Journal of Immunological Methods, 89 (1986), pp. 271–277.

Primary Examiner—Evelyn Mei Huang
(74) Attorney, Agent, or Firm—Rosenthal & Osha L.L.P.

(57) ABSTRACT

A composition includes a substituted dihydro- or tetrahydro-β-carboline of formula (II) or (III), wherein the aromatic ring of the carboline may include one or more substituents selected from the group consisting of hydroxy, $C_{1-6}$ alkoxy, benzyloxy, $C_{1-6}$ acyloxy, amino, $C_{1-6}$ alkyl, $C_{1-6}$ dialkylamino, halogen, and carboxy, and the C-1 position of the carboline may include a substitutent selected from the group consisting of a carbocyclic group and a heterocyclic group. The composition may include a salt or a prodrug of the substituted dihydro- or tetrahydro-β-carboline. The composition may further includes a pharmaceutically acceptable carrier, diluent, or excipient.

6 Claims, 9 Drawing Sheets

Effect of Compound (29) on HepG2/A2 Cell Cycle Distribution

| Time (h) | Treatment 0.8 μM compound (29) | % G0/G1 | S | G2/M | Cell number (x10$^4$) |
|---|---|---|---|---|---|
| 24 | - | 61.5 | 27.6 | 10.9 | 20 |
|  | + | 50.1 | 18.2 | 31.7 | 15 |
| 48 | - | 69.7 | 19.3 | 11.4 | 40 |
|  | + | 55.2 | 18.1 | 26.8 | 15 |
| 72 | - | 66.6 | 25.1 | 8.2 | 47 |
|  | + | 56.3 | 19.5 | 24.2 | 13 |

HepG2/A2 cells were incubated with (+) or without (-) 0.8 μM compound (29) in SF medium. Cells were harvested, and DNA content was measured by flow cytometry.

FIG. 4

Effects of Compound (29) on HeLa Cell Cycle Distribution after the Cells Were Synchronized at G0/G1 Phase

| Time (h) | Treatment 4 μM compound (29) | % G0/G1 | S | G2/M | Cell number (x10$^4$) |
|---|---|---|---|---|---|
| 0 | - | 54.7 | 31.5 | 13.8 | 33 |
| 4 | - | 51.2 | 33.3 | 15.5 | 85 |
|  | + | 47.5 | 36.4 | 16.2 | 99 |
| 8 | - | 44.2 | 39.1 | 16.7 | 131 |
|  | + | 41.1 | 39.9 | 19.1 | 111 |
| 12 | - | 43.4 | 36.9 | 18.7 | 149 |
|  | + | 44.6 | 47.8 | 7.6 | 128 |
| 16 | - | 54.7 | 31.4 | 14.4 | 155 |
|  | + | 48.3 | 28.4 | 23.6 | 146 |

HeLa cells were synchronized at G0/G1 phase as described in Materials and Methods. Cells were incubated with (+) or without (-) 4 μM compound (29) in CM medium. Cells were harvested and DNA content was measured by flow

FIG. 5

Effects of Compound (29) on HeLa Cell Cycle Distribution after the Cells Were Synchronized at G1/S Border

| Time (h) | Treatment 4 μM compound (29) | % G0/G1 | S | G2/M | Cell number (x10$^4$) |
|---|---|---|---|---|---|
| 0 | - | 79.8 | 18.1 | 2.1 | 38 |
| 4 | - | 13.4 | 80.0 | 6.5 | 76 |
|   | + | 3.1 | 87.2 | 9.7 | 59 |
| 8 | - | 15.7 | 20.6 | 63.7 | 70 |
|   | + | 8.2 | 16.1 | 75.7 | 60 |
| 12 | - | 80.1 | 11.1 | 8.8 | 87 |
|   | + | 57.5 | 8.2 | 34.3 | 85 |
| 16 | - | 76.9 | 15.1 | 7.9 | 111 |
|   | + | 84.9 | 8.2 | 6.9 | 86 |

HeLa cells were synchronized at G1/S border as described in Materials and Methods. Cells were incubated with (+) or without (-) 4 μM compound (29) in CM medium. Cells were harvested and DNA content was measured by flow cytometry.

FIG. 6

Effects of Compound (29) on HeLa Cell Cycle Distribution after the Cells Were Synchronized at M Phase

| Time (h) | Treatment 4 µM compound (29) | % GO/G1 | S | G2/M | Cell number (x10⁴) |
|---|---|---|---|---|---|
| 0 | - | 0.7 | 5.3 | 93.9 | 39 |
| 4 | - | 87.4 | 4.2 | 8.5 | 46 |
|   | + | 47.8 | 0.0 | 52.2 | 33 |
| 8 | - | 81.9 | 18.2 | 0.0 | 58 |
|   | + | 60.0 | 8.3 | 31.7 | 33 |
| 12 | - | 10.1 | 69.1 | 20.8 | 55 |
|   | + | 35.1 | 52.2 | 12.7 | 30 |
| 16 | - | 27.9 | 25.4 | 46.8 | 55 |
|   | + | 22.2 | 46.5 | 31.3 | 22 |

HeLa cells were synchronized at M phase as described in Materials and Methods. Cells were incubated with (+) or without (-) 4 µM compound (29) in CM medium. Cells were harvested and DNA content was measured by flow cytometry.

FIG. 7

1-SUBSTITUTED 1,2,3,4-TETRAHYDRO-β-CARBOLINE AND 3,4-DIHYDRO-β-CARBOLINE AND ANALOGS AS ANTITUMOR AGENTS

RELATED APPLICATION

The invention claims priority from Provisional Application Serial No. 60/281,531, filed on Apr. 3, 2001.

BACKGROUND OF INVENTION

1. Field of the Invention

The present invention relates generally to carboline derivatives. In particular the present invention relates to 1-substituted 1,2,3,4-tetrahydro-β-carboline and 3,4-dihydro-β-carboline derivatives which may have useful therapeutic activity, particularly anti-mitotic activity. The present invention also relates to the use of these compounds in therapy and to compositions containing them.

2. Background Art

Despite the increasing research efforts directed towards their treatment and cure, cancerous conditions remain one of the major causes of human mortality. Current clinical treatments include radiation or chemotherapy, or combinations of both. However, in many cases chemotherapy plays a vital role in cancer treatment. The development of various chemotherapeutic drugs which are presently in clinical use has generally been on the characterization of the proliferative cancer cells. The effect of these drugs is to inhibit proliferation of the cancer cells. The chemotherapeutic drugs which are currently used in clinics can be classified into five groups according to their mechanisms of action. They are: (1) alkylating agents, (2) antimetabolites, (3) antibiotics, (4) steroids, and (5) plant alkaloids. The effect of first four groups is considered to occur at the DNA level. The effect of the last group, plant alkaloids, is considered to occur at protein level. During cell proliferation, the chromosome segregation is towed by the mitotic spindle. Therefore, disrupting the formation of the mitotic spindle, can inhibit cell proliferation. Compounds which inhibit cell proliferation by disrupting the formation of the mitotic spindle are called antimitotic agents.

The mitotic spindle is a microtubule-based structure and a cytoskeleton protein. In addition to forming the spindle fibre at mitosis, the mitotic spindle is also involved in intracellular transport, motility architecture (Dumontet, C. et al, *J. Clin. Oncol.*, 17(3), 1061–1070, 1999 and Alberts, B., et al, *Molecular Biology of the Cell*, 3$^{rd}$ "Edition, 807–813, 1994). Microtubules are composed of α, β, tubulin dimer and microtubule associated proteins. The microtubule structure is a dynamic structure with a rapid turnover rate, its half-life being only about 10 minutes. The polymer and tubulin dimer are always in an unstable equilibrium with polymerisation and depolymerisation of microtubules continually and dynamically taking place. The process must go through a course of nucleation, when the tubulin dimer polymerises into a microtubule. In most cells the centrosome is the center of microtubule organizations. After nucleation, polymerisation (lengthening) starts along the cellular periphery. Depolymerisation (shortening) will then occur shortly after polymerisation (it shrinkages back to centrosome). This can result in partial depolymerisation of microtubules that revert to a polymerisation status or the disappearance and replacement with a new microtubule. The process of alternate polymerisation and depolymerisation is called dynamic instability, and this plays an important role in microtubule function. For instance, some proteins inhibit dynamic instability of microtubules thereby inhibiting depolymerisation when cells differentiate into certain morphologies. Mitosis and cytokinesis of normal cells also depend on dynamic instability. Both of rates of polymerisation and depolymerisation of microtubules accelerate at M phase. During mitosis, microtubules rapidly assemble the mitotic spindle. The mitotic spindles subsequently disassembles along the pores of spindle to complete mitosis. Thus, disruption of the dynamic instability of the microtubules, call prevent mitosis and cellular proliferation. The new direction for cancer treatment research is to find new drugs that disrupt the dynamic instability of microtubules.

At present, the antimitotic agents used in the clinic include colchicine, vinca alkaloids and taxol. All of these are natural products. Colchicine and vinca alkaloids can stimulate microtubule depolymerisation. However, the cytotoxicity of colchicine towards healthy cells restricted its development as a widespread therapeutic and its current use is in the treatment of gout. Taxol also disrupts the dynamic instability of the microtubular structure but acts in an opposite manner to colchicine by stimulating tubulin polymerisation and stabilizing microtubules. Many of the antimitotic agents currently under investigation, such as combratastatins, curacins, dolastatin 10, 15, cryptophycins, exhibit antiproliferative mechanisms similar to colchicine or vinca alkaloids. A few, such as discodermolide, epothilones, eleutherobin and laulimalides, exhibit taxol-like effects.

Marine natural products which contain a β-carboline skeleton are widely distributed in marine invertebrates (Blackman, A. J., et al, *J Nat. Prod.*, 1987, 50, 494; Kearns, P. S., et al, *J Nat. Prod.*, 1995, 58, 1075; Kobatashi, J., *J Nat. Prod.*, 1994, 57, 1737). A number of these have been shown to exhibit antitumor and antiviral activity. Particularly interesting compounds include the eudistomins (Badre, A., et al, *J Nat. Prod.*, 1994, 57, 528 and Rinehart Jr, K. L., et al, *J Am., Chem. Soc.*, 1987, 109, 3378) and manzamines (Crews, P., et al, *Tetrahedron*, 1994, 50, 13567 and Sakai, R., et al *Tetrahedron*, 1987, 28, 5493) which were isolated from marine tunicates and sponges, respectively. As a class, the oxathiazepine containing eudistomines exhibited potent inhibitory activity toward DNA virus HSV-1. In addition, the antiviral eudistomines C (1) and E (2) were also found active against HSV-2, the Vaccinia virus and RNA viruses. The novel structures of manzamines, however, were reported to possess potent antitumor activity (Ichiba, T., et al, *Tetrahedron Lett.*, 1988, 29, 3083 and Higa, T., *Studies in Natural Product Chemistry*, Vol. 5, Part B, Elsevier Co., New York, 1989, pp346–353). The most active was manzamine A (3), a principal metabolite from several species of sponges, which showed cytotoxicity against murine P-388 cells at 0.07 µg/ml (Sakai, R., et al, *J Am. Chem., Soc.*, 1986, 108, 6404).

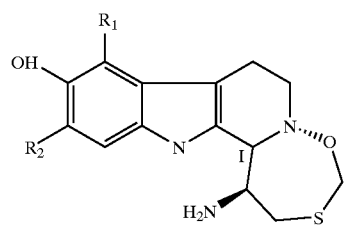

-continued

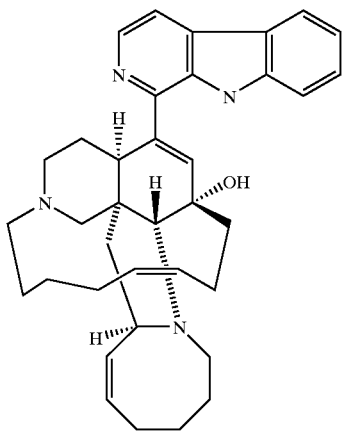

1 R₁—H, R₂= Br
2 R₁—Br, R₂= H

1-Substituted 1,2,3,4-tetrahydro-β-carboline and 3,4-dihydro-β-carboline derivatives have now been prepared and have been shown to exhibit biological activity.

These compounds may, therefore, be useful in the treatment of cancerous conditions.

SUMMARY OF INVENTION

Throughout the specification and the claims which follow, the word "comprise," and variations such as "comprises" and "comprising," will be understood to imply the inclusion of a stated integer, element, or step, or group of integers, elements, or steps, but not the exclusion of any other integer, element, or step, or group of integers, elements, or steps.

In a first aspect, the present invention provides a compound of formula (I).

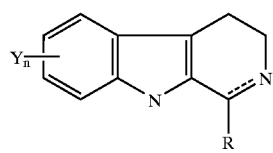

(I)

wherein ---- is an optional double bond, Y comprises one selected from hydroxy, $C_{1-6}$ alkoxy, benzyloxy, $C_{1-6}$ acyloxy, amino, $C_{1-6}$ alkyl, $C_{1-6}$ dialkylamino, halogen and carboxy, and n is 0, 1, 2, 3, or 4, and R comprises one selected from the group consisting of an optionally substituted carbocyclyl ("carbocyclic") group or an optionally substituted heterocyclyl ("heterocyclic") group; or a salt or prodrug thereof.

In another aspect, the invention relates to a composition comprising a compound according to formula (I), or a salt or prodrug thereof, together with a pharmaceutically acceptable carrier, diluent or excipient.

In yet another aspect, the invention relates to a method for the treatment of a cancerous condition comprising the administration of a treatment effective amount of a compound of formula (I) or a pharmaceutically acceptable salt or prodrug thereof, to a subject in need of said treatment.

The invention further provides for the use of a compound of formula (I), or a salt or prodrug thereof, in the manufacture of a medicament for the treatment of a cancerous condition.

The invention also provides an antitumor agent comprising a compound of formula (I) or a pharmaceutically acceptable salt or prodrug thereof.

Other aspects and advantages of the invention will be apparent from the following description and the appended claims.

BRIEF DESCRIPTION OF DRAWINGS

FIG. 4 depicts the effects of (29) on cell cycle distribution. HepG2/A2 cells were cultured in the absence or presence of 0.825 μM (29) for 24, 48, and 72 hours.

FIG. 5 depicts the effects of (29) on cell cycle distribution for HeLa cells treated in the absence or presence of 4 μM (29) for 4, 8, 12, and 16 hours.

FIG. 6 depicts the cell cycle progression for HeLa cells which had been synchronised at the G1/S boundary phase by treatment with 2 mM hydroxyurea for 14–16 hours. After release, the cells were incubated with 4 μM (29) containing medium or drug free medium for 4, 8, 12, and 16 hours.

FIG. 7 depicts the cell cycle progression of HeLa cells which were synchronised at the M phase by treatment with 0.7 μM nocodazole for 16 hours. After release, the cells were incubated in 4 μm (29) containing medium or drug-free medium for 4, 8, 12, and 16 hours.

DETAILED DESCRIPTION

Figure 1:
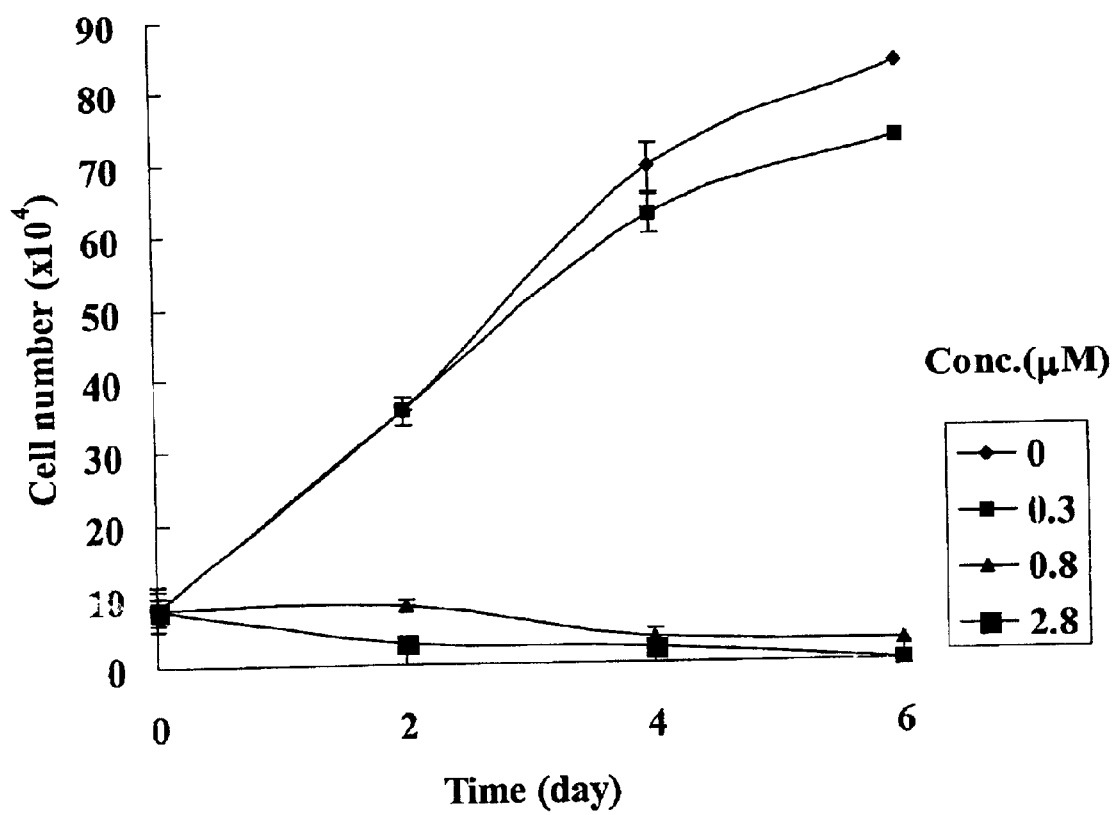
FIG. 1 graphically depicts the long term effect of Compound (29) on the growth of HepG2/A2 cells which were treated with various concentrations of (29).

As used herein, the term "carbocyclyl," "carbocyclic," or "carbocyclo" refers to single, polynuclear, conjugated, or fused cyclic hydrocarbon residues, optionally having one or more double bonds. A carbocyclic group may be non-aromatic or aromatic. Aromatic carbocyclic groups may also be referred to herein as "aryl." Aromatic heterocyclyl groups may be referred to as "heteroaryl."

Examples of carbocyclyl include mono-, bi- and tri-cyclic carbocyclyl residues such as: $C_5$–$C_8$ mono-carbocyclyl (e.g. phenyl, cyclopentyl, cyclohexyl, cycloheptyl, cyclopentenyl, cyclohexenyl, cycloheptenyl, cyclopentadienyl, cyclohexadienyl, cycloheptadienyl, cycloheptatrienyl); $C_8$–$C_{12}$ bi-carbocyclyl (e.g., biphenyl, naphthyl, indenyl, isoindenyl, tetrahydronaphthyl, dihydroindenyl, tetralinyl, decalinyl, pentalenyl, azulenyl) and $C_{12}$–$C_{14}$ tri-carbocyclyl (e.g., anthracenyl, fluorenyl, phenanthrenyl, dihydroanthracenyl, biphenylene, indacenyl). Particularly preferred carbocyclyl are aryl, such as phenyl, and fluorenyl preferably attached at the 2-position).

The term "heterocyclyl," heterocyclic,"" or "heterocyclo" refers to single, fused, conjugated or polynuclear cyclic hydrocarbon residues, optionally having one or more double bonds, wherein a carbon atom is replaced with a heteroatom.

Examples of heteroatoms include O, N and S. A heterocyclyl group may be non-aromatic, or aromatic ("heteroaryl"). Exemplary heterocyclyl groups include: unsaturated 3 to 6 membered heteromonocyclic groups containing 1 to 4 nitrogen atoms, for example, pyrrolyl, pyrrolinyl, imidazolyl, imidazolinyl, pyrazolyl, pyridyl, pyrimidinyl, pyrazinyl, pyridazinyl, triazolyl or tetrazolyl; saturated 3 to 6-membered heteromonocyclic groups containing 1 to 4 nitrogen atoms, such as, pyrrolidinyl, imidazolidinyl, piperidyl, pyrazolidinyl or piperazinyl; condensed saturated or unsaturated heterocyclic groups containing 1 to 5 nitrogen atoms, such as, indolyl, isoindolyl, indolinyl, isoindolinyl, indolizinyl, isoindolizinyl, benzimidazolyl, quinolyl, isoquinolyl, indazolyl, benzotriazolyl, purinyl, quinazolinyl, quinoxalinyl, phenanthradinyl, phenathrolinyl, phthalazinyl, naphthyridinyl, cinnolinyl, pteridinyl, perimidinyl, carbazolyl, acridinyl or tetrazolopyridazinyl; saturated 3 to 6-membered heteromonocyclic groups containing 1 to 3 oxygen atoms, such as tetrahydrofuranyl, tetrahydropyranyl, tetrahydrodioxinyl, unsaturated 3 to 6-membered hetermonocyclic group containing an oxygen atom, such as, pyranyl, dioxinyl or furyl; condensed saturated or unsaturated heterocyclic groups containing 1 to 3 oxygen atoms, such as benzofuranyl, chromenyl or xanthenyl; unsaturated 3 to 6-membered heteromonocyclic group containing 1 to 2 sulphur atoms, such as, thienyl or dithiolyl; unsaturated 3 to 6-membered heteromonocyclic group containing 1 to 2 oxygen atoms and 1 to 3 nitrogen atoms, such as, oxazolyl, oxazolinyl, isoxazolyl, furazanyl or oxadiazolyl; saturated 3 to 6-membered heteromonocyclic group containing 1 to 2 oxygen atoms and 1 to 3 nitrogen atoms, such as, morpholinyl; unsaturated condensed heterocyclic group containing 1 to 2 oxygen atoms and 1 to 3 nitrogen atoms, such as, benzoxazolyl or benzoxadiazolyl; unsaturated 3 to 6-membered heterormonocyclic group containing 1 to 2 sulphur atoms and 1 to 3 nitrogen atoms, such as, thiazolyl, thiazolinyl or thiadiazoyl; saturated 3 to 6-membered heteromonocyclic group containing 1 to 2 sulphur atoms and 1 to 3 nitrogen atoms, such as, thiazolidinyl, thiomorphinyl; and unsaturated condensed heterocyclic group containing 1 to 2 sulphur atoms and 1 to 3 nitrogen atoms, such as, benzothiazolyl or benzothiadiazolyl.

A preferred heterocyclyl group is heteroaryl, such as carbazolyl, preferably attached at the 3-position.

A carbocyclyl or heterocyclyl group may be optionally substituted, at a carbon or, where appropriate, nitrogen atom by one or more optional substituents. Suitable optional substituents may include halo (fluoro, chloro, bromo, iodo), hydroxy, $C_{1-8}$ straight or branched alkyl (e.g., methyl, ethyl, n-propyl, isopropyl, n-butyl, sec-butyl, t-butyl, n-pentyl, isopentyl, etc), $C_{1-8}$ alkoxy (e.g., methoxy, ethoxy, n-propoxy, iso-propoxy, n-butoxy, sec-butoxy, t-butoxy, etc), amino, $C_{1-8}$ alkylamino (e.g., methylamino, ethylamino, n-propylamino, isopropylamino), $C_{1-8}$ dialkylamino (e.g., dimethylamino, diethylamino, dipropylamino, diisopropylamino), $C(O)C_{1-6}$ alkyl ("carbonyl," e.g., acetyl, C(O)ethyl, C(O)propyl), $OC(O)C_{1-8}$ alkyl ("carbonyloxy," e.g., acetoxy), carboxylic acid, $CO_2C_{1-8}$ alkyl ("ester," e.g., methyl ester, ethyl ester), benzyl (wherein the $CH_2$ or phenyl group thereof may be further optionally substituted), phenyl (which itself may be further optionally substituted), $CONH_2$, $CONHC_{1-8}$ alkyl (e.g., methylamide, ethylamide), acetyl, benzoyl (wherein the phenyl group may be further optionally substituted), keto (where a $CH_2$ group is replaced with C=O), hydro (where a HC=CH— group is replaced by —$CH_2$—$CH_2$—), nitro, dimethyleneoxy, mercapto, $C_{1-8}$ alkylthio (e.g., SMe, SEt etc).

Thus, in a preferred embodiments of the invention, R is a phenyl group optionally substituted by one or more of: chloro, bromo, nitro, dialkylamine (e.g., dimethy-, diethyl-, or dipropyl (n-or iso-) amine), methoxy, ethoxy, n-propoxy, iso-propoxy, butoxy (n-, sec-, or t-), dimethyleneoxy, hydroxy, acetoxy.

Where a heterocyclyl group contains an sp3 nitrogen atom, preferably this may be optionally substituted by $C_{1-6}$ alkyl (e.g., methyl, ethyl, propyl) or $C(O)C_{1-6}$ alkyl (e.g., acetyl, C(O)ethyl, C(O)propyl).

A preferred R group is carbazolyl N-substituted by methyl, ethyl or propyl, butyl, pentyl, octyl, (preferably ethyl) or acetyl.

In a preferred form, the compounds of Formula (I) are presented in the form of a salt or prodrug, which may enhance solubility or bioavailability of the compound. The term "salt or prodrug" includes any pharmaceutically acceptable salt, ester, solvate, hydrate or any other compound which, upon administration to the recipient is capable of providing (directly or indirectly) a compound as described herein. However, it will be appreciated that non-pharmaceutically acceptable salts also fall within the scope of the invention since these may be useful in the preparation of pharmaceutically acceptable salts.

Suitable pharmaceutically acceptable salts include, but are not limited to salts of pharmaceutically acceptable inorganic acids such as hydrochloric, sulphuric, phosphoric nitric, carbonic, boric, sulfamic, and hydrobromic acids, or salts of pharmaceutically acceptable organic acids such as acetic, propionic, butyric, tartaric, maleic, hydroxymaleic, fumaric, maleic, citric, lactic, mucic, gluconic, benzoic, succinic, oxalic, phenylacetic, methanesulphonic, toluenesulphonic, benezenesulphonic, salicyclic sulphanilic, aspartic, glutamic, edetic, stearic, palmitic, oleic, lauric, pantothenic, tannic, ascorbic and valeric acids.

Base salts include, but are not limited to, those formed with pharmaceutically acceptable cations, such as sodium, potassium, lithium, calcium, magnesium, aminonium and alkylammonium.

Basic nitrogen-containing groups may be quarternised with such agents as lower alkyl halide, such as methyl, ethyl, propyl, and butyl chlorides, bromides and iodides; dialkyl sulfates like dimethyl and diethyl sulfate; and others.

The compounds of the invention may be in crystalline form either as the free compounds or as solvates (e.g. hydrates) and it is intended that both forms are within the scope of the present invention. Methods of salvation are generally known within the art.

Any compound that is a prodrug of a compound of formula (I) is within the scope and spirit of the invention. The term "pro-drug" is used in its broadest sense and encompasses those derivatives that are converted in vivo to the compounds of the invention. Such derivatives would readily occur to those skilled in the art, and include, for example, compounds where a free hydroxy group is converted into an ester, such as an acetate, or where a free amino group is converted into an amide (for example by acylation). Procedures for acylating the compounds of the invention are well known in the art and may include treatment of the compound with an appropriate carboxylic acid, anhydride or chloride in the presence of a suitable catalyst or base.

In yet another aspect, the invention relates to a method for the treatment of a cancerous condition comprising the administration of a treatment effective amount of a compound of the invention or a pharmaceutically acceptable salt or prodrug thereof, to a subject in need of said treatment.

The invention also provides a method of inducing apoptosis in a cell, particularly a cancerous cell, comprising contacting said cell with an effective amount of a compound of the invention for a time and under conditions sufficient to induce cell death.

The term "cancer" as used in "cancerous condition" is used in its broadest sense and includes benign and malignant leukemia, sarcomas and carcinomas as well as other neoplasia. Cancerous or tumorous conditions which may be treated by the compounds of the invention may be simple (monoclonal, i.e., composed of a single neoplastic cell type), mixed (polyclonal, i.e., composed of more than one neoplastic cell type and derived from more than one germ layer). Some examples of cancerous conditions which may be treated include breast, colon, uterus, prostate, lung, ovarian, skin, mouth, throat, liver, and stomach cancers, tumors and melanomas. As used herein, "cancerous condition" is also intended to refer to conditions which are precursors to a cancerous conditions, i.e., precancerous conditions.

The compounds of the invention may be used to treat humans or other mammalian subjects. The compounds of the invention are considered to be particularly suitable for the treatment of human subjects. Non-human subjects may include primates, livestock animals (e.g., sheep, cows, horses, goats, pigs) domestic companion animals (e.g., cats, dogs) laboratory test animals (e.g., mice, rats, guinea pigs, rabbits) or captive wild animals.

The compounds of the invention are administered to the subject in a treatment effective amount. As used herein, a treatment effective amount is intended to include at least partially attaining the desired effect, or delaying the onset of, or inhibiting the progression of, or halting or reversing altogether the onset or progression of the particular cancerous condition or pre-cancerous condition being treated, according to a desired dosing regimen.

As used herein, the term "effective amount" relates to an amount of compound which, when administered according to a desired dosing regimen, provides the desired therapeutic activity. Dosing may occur at intervals of minutes, hours, days, weeks, months or years or continuously over any one of these periods. Suitable dosages lie within the range of about 0.1 ng per kg of body weight to 1 g per kg of body weight per dosage. The dosage is preferably in the range of 1 µg to 1 g per kg of body weight per dosage, such as is in the range of 1 mg to 1 g per kg of body weight per dosage. In one embodiment, the dosage is in the range of 1 mg to 500 mg per kg of body weight per dosage. In another embodiment, the dosage is in the range of 1 mg to 250 mg per kg of body weight per dosage. In yet another preferred embodiment, the dosage is in the range of 1 mg to 100 mg per kg of body weight per dosage, such as up to 50 mg per kg of body weight per dosage.

One skilled in the art would appreciate that suitable dosage amounts and dosing regimens may be determined by the attending physician and may depend on the particular condition being treated, the severity of the condition, as well as the general health, age and weight of the subject.

The active ingredient may be administered in a single dose or a series of doses.

While it is possible for the active ingredient to be administered alone, it is preferable to present it as a composition, preferably as a pharmaceutical composition. The formulation of such compositions is well known to those skilled in the art. The composition may contain any suitable carriers, diluents or excipients. These include all conventional solvents, dispersion media, fillers, solid carriers, coatings, antifungal and antibacterial agents, dermal penetration agents, surfactants, isotonic and absorption agents and the like. It will be understood that the compositions of the invention may also include other supplementary physiologically active agents The carrier must be pharmaceutically "acceptable" in the sense of being compatible with the other ingredients of the composition and not injurious to the subject. Compositions include those suitable for oral, rectal, nasal, topical (including buccal and sublingual), vaginal or parenteral (including subcutaneous, intramuscular, intravenous and intradermal) administration. The compositions may conveniently be presented in unit dosage form and may be prepared by any methods well known in the art of pharmacy. Such methods include the step of bringing into association the active ingredient with the carrier which constitutes one or more accessory ingredients. In general, the compositions are prepared by uniformly and intimately bringing into association the active ingredient with liquid carriers or finely divided solid carriers or both, and then if necessary shaping the product.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder (e.g., inert diluent, preservative disintegrant (e.g. sodium starch glycolate, cross-linked polyvinyl pyrrolidone, cross-linked sodium carboxymethyl cellulose) surface-active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured base, usually sucrose and acacia or tragacanth gum; pastilles comprising the active ingredient in an inert basis such as gelatin and glycerin, or sucrose and acacia gum; and mouthwashes comprising the active ingredient in a suitable liquid carrier.

Compositions for topical administration, for example, to the skin, may be in the form of ointments, pastes, creams, gels, lotions, powders and the like and may include additional agents such as dermal penetration enhancers.

Compositions for rectal administration may be presented as a suppository with a suitable base comprising, for example, cocoa butter, glycerin, polyethylene glycol or gelatin.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bactericides and solutes which render the composition isotonic with the blood of the intended recipient; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as herein above described, or an appropriate fraction thereof, of the active ingredient.

It should be understood that in addition to the active ingredients particularly mentioned above, the compositions of this invention may include other agents conventional in the art having regard to the type of composition in question. For example, those suitable for oral administration may include such further agents as binders, sweeteners, thickeners, flavouring agents disintegrating agents, coating agents, preservatives, lubricants and/or time delay agents. Suitable sweeteners include sucrose, lactose, glucose, aspartame or saccharine. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

The compounds of the invention can be prepared in accordance with the -procedure outlined in Scheme I.

Scheme I

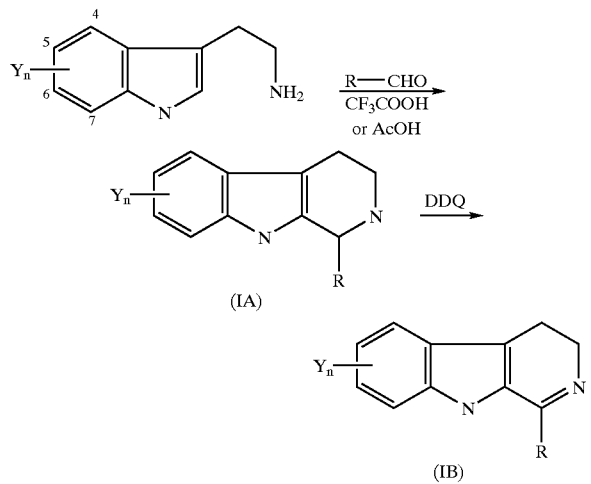

Thus, for example, Pictet-Spongler reaction (Valentine Jr D., et al, *Synthesis*, 1978, 329 and Kawashima, Y., et al, *Chem. Pharm. Bull.*, 1995, 43, 329) by treatment of tryptamine with an appropriate aldehyde in the presence of trifluroacetic acid or acetic acid affords access to compounds of formula (IA). Subsequent oxidation, such as by treatment with DDQ (Kondo, K., et al, *J Org. Chem.*, 1992, 57, 2460), affords access to the compounds of formula (IB).

It will be understood that the aromatic benzene ring of the starting tryptamine compound may be optionally substituted at one or more of the 4-, 5-, 6-, and 7-positions by a substituent. Suitable substituents may include hydroxy, $C_{1-6}$ alkoxy (e.g., methoxy, ethoxy, propoxy), benzyloxy $C_{1-6}$ acyloxy (e.g., OC(O)Me, OC(O)Et), amino, $C_{1-6}$ alkyl, $C_{1-6}$ dialkylamino, halogen (i.e., Br, Cl, I or F) or carboxy. A preferred substitution position is the 5- or 6-position, for example a 5- or 6-oxy substituted tryptamine such as 5- or 6-hydroxytryptamine (which may be alkylated or acetylated using known procedures) or 5- or 6-methoxy tryptamine. Some substituted starting tryptamines are commercially available (e.g., 5- and 6-hydroxy and 5- and 6-methoxy tryptamine). In a particularly preferred form, such substituted compounds of formula (1) also include compounds of the formula:

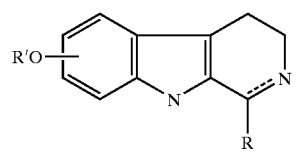

Wherein ⚏ and R are as herein described and R' is H, $C_{1-6}$ alkyl, $C_{1-6}$ acyl or benzyl.

Other compounds bearing a substituted aromatic ring may be prepared by the synthesis of suitably substituted indoles, for example, by Fischer indole synthesis using an appropriately substituted phenyl hydrazone or by electrophillic aromatic substitution of a suitably protected form of (IA) or (IB).

Those skilled in the art will appreciate that the invention described herein is susceptible to variations and modifications other than those specifically described. It is to be understood that the invention includes all such variations and modifications which fall within the spirit and scope. The invention also includes all of the steps, features, compositions and compounds referred to or indicated in this specification, individually or collectively, and any and all combinations of any two or more of said steps or features.

The invention will now be described with reference to the following examples which are included for the purpose of illustrating the invention and are not to be construed as limiting the generality hereinbefore described.

EXAMPLES

Example 1

General Methods for the Preparation of Compounds of Formula (I)

All melting points were taken on a Buchi mp B-540 apparatus and were uncorrected. UV and IR spectra were taken on a Hitachi V-3210 and JASCO A-100 IR spectrophotometers, respectively. EIMS spectra were obtained on a MAT 112S-JMS D300 spectrometer, using direct inlet systems. $^1$H- and $^{13}$C-NMR spectra were recorded on a Varian FT-300 spectrometer. Analytical thin-layer chromatography (TLC) was carried out on Kiesel gel $GF_{254}$ coated plates and detection was made under UV light.

EM Kieselgel 60 (230–400 mesh ASTM) was used for column chromatography.

General Procedure for the Synthesis of Compounds 4–16 (Formula IA)

To a stirred solution of tryptamine (1.6 g, 1 mmol) and the appropriate substituted aldehyde (1 mmol) in toluene (30 ml) at room temperature was slowly added trifluoroacetic acid (TFA, 2 ml). The reaction mixture was stirred at room temperature for two days. After evaporation of the solvent under vacuum, the residue was chromatographed on a silica gel column (60 g) and eluted with solvent mixture of $CHCl_3/MeOH$ by the following ratios and volumes (99:1, 98:2, 97:3, 96:4 and 95:5; each 100 ml), to afford compounds 4–16 with yields which varied in a range of 30–50%.

A mixture of tryptamine (1.6 g, 1 mmol) and the appropriate substituted aldehyde (1 mmol) in acetic acid (50 ml) was reacted at 100° C. overnight. The reaction product was added $H_2O$ (200 ml) and the $H_2O$ suspension was extracted with $CHCl_3$ soluble layer. After evapouration of the solvent under vacuum, the residue was chromatographed on a Si gel column (150 g) and eluted with solvent mixture of $CHCl_3/MeOH$ (15:1, 600 ml), to afford compounds 4–16 with yields in the range of 60–90%.

In a similar manner, 5-methoxy and 6-methoxy tryptamine may be used. Thus, to a stirred solution of 5-methoxy or 6-methoxy tryptamine (0.17 g, 0.1 mmol) and the appropriate aldehyde (1 mmol) in toluene (5 ml) is added TFA (0.3 ml), slowly at room temperature. The mixture is stirred at room temperature for two days. Following evaporation of the solvent under vacuum, the residue can be chromatographed as above.

General Procedure for the Synthesis of Compounds 17–29 (Formula IB)

To a stirred solution of compound of Formula 1A (4–16, 0.03 mmol) in ETOH (1 ml) and $CHCl_3$ (3 ml) at room temperature was added 2,3-dichloro-5,6-dicyanobenzoquinone (DDQ, 40 mg). The reaction mixture was stirred for 30 minutes.

After concentration, the residue was applied on a preparative TLC plate and developed with $CHCl_3/MeOH$ (10:1) to yield compound 17–29.

Example 1a 1-(4'-Chlorophenyl)-1,2,3,4-tetrahydro-β-carboline (4)

White solid; $C_{17}H_{15}N_2Cl$; $^1$H-NMR ($CDCl_3$) δ 5.09 (1H, s, H-1), 3.11 (1H, m, H-3a), 3.28 (1H, m, H-3b), 2.85 (2H, m, H-4), 7.17 (3H, overlap, H-5, 6, 7), 7.57 (1H, d, J=8.4 Hz, H-8), 7.87 (1H, s, NH-9), 7.20 (2H, d, J=7.8 Hz, H-2', 6'), 7.31 (2H, d, J=7.8 Hz, H-3', 5'); $^{13}$C-NMR ($CDCl_3$) δ 57.1 (d, C-1), 42.2 (t, C-3), 22.3 (t, C-4), 110.2 (s, C-4a), 133.7 (s, C-4b), 121.8 (d, C-5), 119.4 (d, C-6), 118.2 (d, C-7), 110.8 (d, C-8), 140.3 (s, C-8a), 135.9 (s, C-9a), 127.2 (s, C-1'), 129.8 (d, C-2', 6'), 128.9 (d, C-3', 5'), 133.9 (s, C-4'); EIMS m/z 285 (6), 284 (34), 283 (100, M$^+$), 281 (72), 255 (13), 254 (17), 253 (39), 252 (30), 219 (25), 218 (92), 217 (80), 189 (9), 171 (81), 169 (18), 154 (9), 144 (21), 143 (20), 130 (10), 123 (15), 115 (22), 109 (51).

Example 1b 1-(4'-Bromophenyl)-1,2,3,4-tetrahydro-β-carboline (5)

$C_{17}H_{15}N_2Br$; $^1$H-NMR ($CDCl_3$) δ 5.10 (1H, s, H-1), 3.12 (1H, m, H-3a), 3.30 (1H, m, H-3b), 2.87 (2H, m, H-4), 7.18 (3H, overlap, H-5, 6, 7), 7.65 (1H, d, J=6.9 Hz, H-8), 7.74 (1H, s, NH-9), 7.17 (2H, d, J=8.4 Hz, H-2', 6'), 7.47 (2H, d, J=8.4 Hz, H-3', 5'); $^{13}$C-NMR ($CDCl_3$) δ 57.3 (d, C-1), 42.5 (t, C-3), 22.4 (t, C-4), 110.3 (s, C-4a), 133.6 (s, C-4b), 121.9 (d, C-5), 119.4 (d, C-6), 118.2 (d, C-7), 110.8 (d, C-8), 140.8 (s, C-8a), 135.9 (s, C-9a), 127.2 (s, C-1'), 130.2 (d, C-2', 6'), 131.8 (d, C-3',5'), 122.0 (s, C-4'); EIMS m/z 328 (43), 327 (37, M$^+$), 326 (48), 325 (34), 299 (17), 297 (18), 219 (28), 218 (100), 217 (93), 216 (30), 189 (9), 171 (64), 169 (17), 144 (19), 143 (21), 130 (15), 123 (27), 109 (55).

Example 1c 1-(4'-Nitrophenyl)-1,2,3,4-tetrahydro-β-carboline (6)

$C_{17}H_{15}N_3O_2$; $^1$H-NMR ($CDCl_3$) δ 5.28 (1H, s, H-1), 3.17 (1H, m, H-3a), 3.28 (1H, m, H-3b), 2.87 (2H, m, H-4), 7.27 (1H, d, J=7.5 Hz, H-5), 7.17 (2H, t, J=7.5 Hz, H-6,7), 7.57 (1H, d, J=7.5 Hz, H-8), 7.87 (1H, s, NH-9), 7.50 (2H, d, J=8.7 Hz, H-2', 6'), 8.18 (2H, d, J=8.7 Hz, H-3', 5'); $^{13}$C-NMR ($CDCl_3$) δ 57.1 (d, C-1), 42.2 (t, C-3), 22.4 (t, C-4), 110.8 (s, C-4a), 127.1 (s, C-4b), 122.2 (d, C-5), 119.7 (d, C-6), 118.4 (d, C-7), 110.9 (d, C-8), 147.6 (s, C-8a), 135.6 (s, C-9a), 136.0 (s, C-1'), 129.4 (d, C-2', 6'), 123.9 (d, C-3', 5'), 149.3 (s, C-4'); EIMS m/z 293 (82, M$^+$), 292 (45), 264 (31), 247 (20), 218 (80), 217 (100), 216 (38), 204 (11), 189 (10), 171 (68), 169 (13), 154 (8), 144 (17), 143 (20), 130 (11), 115 (21), 109 (23).

Example 1d 1-(4'-Dimethylaminophenyl)-1,2,3,4-tetrahydro-β-carboline (7)

$^1$H-NMR ($CDCl_3$) δ 5.11 (1H, s, H-1), 3.14 (1H, m, H-3a), 3.44 (1H, m, H-3b), 2.84 (2H, m, H-4), 7.56 (1H, d, J=7.0 Hz, H-5), 7.14 (2H, overlap, H-6,7), 7.75 (1H, d, J=7.5 Hz, H-8), 7.17 (2H, d, J=8.4 Hz, H-2', 6'), 6.69 (2H, d, J=8.4 Hz, H-3', 5'), 2.95 (6H, s, NMe$_2$); $^{13}$C-NMR ($CDCl_3$) δ 53.0 (d, C-1), 41.2 (t, C-3), 25.9 (t, C-4), 113.2 (s, C-4a), 127.2 (s, C-4b), 122.1 (d, C-5), 119.5 (d, C-6), 118.8 (d, C-7), 112.0 (d, C-8), 136.4 (s, C-8a), 132.9 (s, C-9a), 122.1 (s, C-1'), 127.4 (d, C-2', 6'), 112.9 (d, C-3', 5'), 149.4 (s, C-4'), 40.7 (q, NMe$_2$).

Example 1e 1-(4'-N-Diethylaminophenyl)-1,2,3,4-tetrahydro-β-carboline (8)

$C_{21}H_{25}N_3$; $^1$H-NMR ($CDCl_3$) δ 5.04 (1H, s, H-1), 3.12 (1H, m, H-3a), 3.40 (1H, m, H-3b), 2.83 (2H, m, H-4), 7.15 (3H, overlap, H-5,6,7), 7.55 (1H, d, J=8.4 Hz, H-8), 8.05 (1H, s, H-9), 7.15 (2H, d, J=9 Hz, H-2', 6'), 6.63 (2H, d, J=9 Hz, H-3', 5'), 1.17 (6H, t, J=7.1 Hz, $CH_2CH_3$), 3.35 (4H, q, J=7.1 Hz, $\underline{CH_2}CH_3$); $^{13}$C-NMR ($CDCl_3$) $\overline{δ}$ 57.3 (d, C-1), 42.7 (t, $\overline{C-3}$), $\overline{22}$.4 (t, C-4), 109.3 (s, C-4a), 127.8 (s, C-4b), 122.3 (d, C-5), 119.0 (d, C-6), 118.0 (d, C-7), 110.8 (d, C-8), 135.7 (s, C-8a), 135.2 (s, C-9a), 127.4 (s, C-1'), 129.5 (d, C-2', 6'), 111.6 (d, C-3', 5'), 147.6 (s, C-4'), 12.5 (t, $CH_2$ $CH_3$), 44.3 (q, $\underline{CH_2}CH_3$); EIMS m/z 319 (96, M$^+$), 318 $\overline{(100)}$, 290 (28), $\overline{289}$ (29), 276 (19), 275 (17), 274 (12), 260 (5), 245 (9), 219 (11), 218 (39), 217 (41), 216 (12), 204 (5), 189 (5), 171 (28), 169 (14), 160 (10), 144 (13), 143 (21), 137 (18), 130 (15), 123 (14), 109 (14).

Example 1f 1-(2',4'-Dimethoxyphenyl)-1,2,3,4-tetrahydro-β-carboline (9)

Pale yellow solid; $C_{19}H_{20}N_2O_2$; IR (KBr) ν max 3410, 2950, 1615, 1505, 1465, 1300, 1160, 1040, 835, 715 cm$^{-1}$;

¹H-NMR (CDCl₃) δ 5.54 (1H, s, H-1), 3.11 (1H, m, H-3a), 3.27 (1H, m, H-3b), 2.84 (2H, m, H-4), 7.23 (1H, d, J=6.8 Hz, H-5), 7.13 (2H, overlap, H-6,7), 7.53 (1H, d, J=6.8 Hz, H-8), 7.78 (1H, s, H-9), 6.53 (1H, d, J=2.4 Hz, H-3'), 6.37 (1H, d, J=8.7, 2.4 Hz, H-5'), 6.93 (1H, d, J=8.7 Hz, H-6'), 3.79, 3.87 (6H, s, OMe); ¹³C-NMR (CDCl₃) δ 50.6 (d, C-1), 42.0 (t, C-3), 22.5 (t, C-4), 110.1 (s, C-4a), 127.4 (s, C-4b), 121.4 (d, C-5), 119.2 (d, C-6), 118.0 (d, C-7), 110.7 (d, C-8), 135.7 (s, C-8a), 134.6 (s, C-9a), 122.3 (s, C-1'), 98.8 (d, C-3'), 104.0 (d, C-5'), 110.7 (d, C-6'), 55.4, 55.6 (q, OMe); EIMS m/z 308 (100, M⁺), 307 (73), 279 (31), 278 (43), 264 (12), 249 (13), 248 (30), 233 (9), 217 (7), 204 (18), 191 (8.4), 171 (38), 154 (17), 143 (21), 130 (13), 115 (15), 102 (13), 95 (9), 77 (13), 69 (22).

Example 1g 1-(3',4'-Dimethoxyphenyl)-1,2,3,4-tetrahydro-β-carboline (10)

Pale yellow solid; $C_{19}H_{20}N_2O_2$; IR (KBr) ν max cm⁻¹; ¹H-NMR (CDCl₃) δ 5.04 (1H, s, H-1), 3.10 (1H, m, H-3a), 3.32 (1H, m, H-3b), 2.89 (2H, m, H-4), 7.12 (3H, overlap, H-5,6,7), 7.56 (1H, d, J=5.7 Hz, H-8), 8.32 (1H, s, H-9), 6.80 (1H, s, H-2'), 6.75 (1H, d, J=8.1 Hz, H-5'), 6.78 (1H, d, J=8.1 Hz, H-6'), 3.70 (3H, s, 3'-OMe), 3.84 (3H, s, 4'-OMe); ¹³C-NMR (CDCl₃) δ 57.9 (d, C-1), 42.9 (t, C-3), 22.3 (t, C-4), 109.7 (s, C-4a), 134.2 (s, C-4b), 121.4 (d, C-5), 120.5 (d, C-6), 119.0 (d, C-7), 111.2 (d, C-8), 135.8 (s, C-8a), 134.5 (s, C-9a), 127.2 (s, C-1'), 110.8 (d, C-2'), 148.6 (d, C-3'), 149.0 (s, C-4'), 110.8 (d, C-5'), 118.0 (d, C-6'), 55.7, 55.6 (q, OMe); EIMS m/z 308 (100, M⁺), 307 (82), 291 (9.4), 279 (19), 264 (8), 249 (15), 248 (43), 233 (9), 217 (9), 204 (20), 191 (11), 171 (64), 154 (20), 143 (16), 130 (9), 115 (12), 102 (14), 95 (9), 77 (8).

Example 1h 1-(2',5'-Dimethoxyphenyl)-1,2,3,4-tetrahydro-β-carboline (11)

Pale yellow solid; $C_{19}H_{20}N_2O_2$; IR (KBr) ν max 3410, 2950, 1680, 1505, 1465, 1135, 1045, 750 cm⁻¹; ¹H-NMR (CDCl₃) δ 5.64 (1H, s, H-1), 3.20 (1H, m, H-3a), 3.32 (1H, m, H-3b), 2.88 (2H, m, H-4), 7.23 (1H, d, J=6.8 Hz, H-5), 7.12 (2H, overlap, H-6,7), 7.52 (1H, d, J=6.8 Hz, H-8), 7.85 (1H, s, H-9), 6.90 (1H, d, J=8 Hz, H-3'), 6.83 (1H, dd, J=8, 2 Hz, H-4'), 6.71 (1H, d, J=2 Hz, H-6'), 3.67, 3.81 (6H, s, OMe); ¹³C-NMR (CDCl₃) δ 51.2 (d, C-1), 42.0 (t, C-3), 21.8 (t, C-4), 109.8 (s, C-4a), 129.7 (s, C-4b), 121.7 (d, C-5), 119.3 (d, C-6), 118.1 (d, C-7), 110.8 (d, C-8), 127.1 (s, C-1'), 111.8 (d, C-3'), 113.6 (d, C-4'), 115.5 (d, C-6'), 55.7, 56.2 (q, OMe); EIMS m/z 308 (100, M⁺), 307 (56), 292 (4), 279 (21), 264 (6), 249 (2), 248 (67), 233 (15), 217 (12), 204 (24), 191 (7.7), 171 (79), 169 (20), 154 (17), 144 (30), 143 (27), 130 (18), 115 (18), 102 (15), 69 (39).

Example 1i 1-(3',5'-Dimethoxyphenyl)-1,2,3,4-tetrahydro-β-carboline (12)

Pale yellow solid; $C_{19}H_{20}N_2O_2$; IR (KBr) ν max 3420, 2910, 1605, 1465, 1350, 1305, 1155, 1065, 845, 785 cm⁻¹; ¹H-NMR (CDCl₃) δ 5.03 (1H, s, H-1), 3.11(1H, m, H-3a), 3.35 (1H, m, H-3b), 2.91 (2H, m, H-4), 7.15 (3H, overlap, H-5,6,7), 7.56 (1H, d, J=7 Hz, H-8), 8.13 (1H, s, H-9), 6.47 (2H, d, J=2.1 Hz, H-2',6'), 6.44 (1H, d, J=2.1 Hz, H-4'), 3.71 (6H, s, OMe); ¹³C-NMR (CDCl₃) δ 58.3 (d, C-1), 43.0 (t, C-3), 22.3 (t, C-4), 109.8 (s, C-4a), 127.3 (s, C-4b), 121.6 (d, C-5), 119.2 (d, C-6), 118.1 (d, C-7), 110.8 (d, C-8), 144.1 (s, C-8a), 135.8 (s, C-9a), 134.2 (s, C-1'), 106.5 (d, C-2',6'), 161.1 (s, C-3',5'), 100.0 (d, C-4'), 55.3 (q, OMe); EIMS m/z 308 (100, M⁺), 307 (64), 279 (38), 278 (37), 264 (11), 249 (17), 248 (30), 233 (10), 220 (9), 217 (9), 204 (21), 191 (10), 171 (85), 154 (13), 144 (17), 130 (10), 115 (16), 102 (13), 95 (9), 77 (10).

Example 1j 1-(3',4',5'-Trimethoxyphenyl)-1,2,3,4-tetrahydro-β-carboline (13)

$C_{20}H_{22}N_2O_3$; ¹H-NMR (CDCl₃) δ 5.85 (1H, s, H-1), 3.59 (1H, m, H-3a), 3.68 (1H, m, H-3b), 3.29 (2H, m, H-4), 7.32 (1H, d, J=8 Hz, H-5), 7.16 (1H, t, J=8 Hz, H-6), 7.11 (1H, J=8 Hz, H-7), 7.55 (1H, d, J=8 Hz, H-8), 6.73 (2H, s, H-2',6'), 3.71 (9H, s, OMe); ¹³C-NMR (CDCl₃) δ 56.1 (d, C-1), 41.7 (t, C-3), 51.5 (t, C-4), 109.4 (s, C-4a), 126.7 (s, C-4b), 122.4 (d, C-5), 119.7 (d, C-6), 118.4 (d, C-7), 111.1 (d, C-8), 136.2 (s, C-8a), 133.3 (s, C-9a), 128.6 (s, C-1'), 106.1 (d, C-2',6'), 153.4 (s, C-3',5'), 153.8 (s, C-4'), 56.1 (q, 3',5'-OMe), 60.7 (q, 4'-OMe); EIMS m/z 338 (100, M⁺), 337 (73), 309 (17), 279 (14), 278 (39), 262 (6.7), 247 (9), 234 (7.8), 219 (6.9), 204 (6.7), 191 (10), 180 (12), 171 (69), 169 (24), 154 (13), 144 (20), 130 (11), 115 (15), 109 (12), 77 (11), 69 (54).

Example 1k:

1-(3'-Nitroz4'-Benzo-1",3"-dioxole)-1,2,3,4-tetrahydro-β-carboline (14)

$C_{18}H_{15}N_3O_4$; ¹H-NMR (CDCl₃)δ5.66 (1H, s, H-1), 3.17 (1H, m, H-3a), 3.25 (1H, m, H-3b), 2.89 (2H, m, H-4), 7.23 (1H, d, J=7.6 Hz, H-5), 7.16 (2H, overlap, H-6,7), 7.56 (1H, d, J=7.6 Hz, H-8), 8.04 (1H, s, H-9), 6.77 (1H, s, H-2'), 7.39 (1H, s, H-5'), 6.01 (2H, d, J=4.2 Hz, O—CH₂-O); ¹³C-NMR (CDCl₃)δ52.4 (d, C-1), 42.0 (t, C-3), 22.1 (t, C-4), 111.1 (s, C-4a), 127.0 (s, C-4b), 122.0 (d, C-5), 119.5 (d, C-6), 118.3 (d, C-7), 110.9 (d, C-8), 136.0 (s, C-8a), 134.1 (s, C-9a), 132.6 (s, C-1'), 109.9 (d, C-2'), 151.7 (s, C-3'), 147.3 (s, C-4'), 104.9 (d, C-5'), 143.7 (s, C-6'), 102.9 (t, O-CH₂-O); EIMS m/z 337 (6, M+), 335 (6.7), 320 (9), 319 (70), 303 (56), 290 (93), 289 (100), 275 (6), 261 (24), 244 (11), 232 (13), 216 (9), 204 (33), 203 (19), 191 (18), 171 (20), 151 (18), 144 (32), 130 (53), 115 (50), 102 (52), 101 (22), 89 (20), 77 (25).

Example 1l 1-(2'-Fluorenyl)-1,2,3,4-tetrahydro-β-carboline (15)

Yellow solid; $C_{24}H_{20}N_2$; IR (KBr) ν max 3540, 2990, 1680, 1710, 1465, 745 cm⁻¹; ¹H-NMR (CDCl₃) δ 5.23 (1H, s, H-1), 3.17 (1H, m, H-3a), 3.41 (1H, m, H-3b), 2.94 (2H, m, H-4); ¹³C-NMR (CDCl₃) δ 58.3 (d, C-1), 43.0 (t, C-3), 22.6 (t, C-4), 110.2 (s, C-4a), 127.5 (s, C-4b), 121.7 (d, C-5), 119.4 (d, C-6), 118.3 (d, C-7), 110.9 (d, C-8), 143.9 (s, C-8a), 134.8 (s, C-9a), 125.1 (s, C-1'), 135.9 (s, C-2'), 125.1 (d, C-3'), 120.0 (d, C-4'), 141.2 (s, C-4'a), 141.8 (s, C-4'b), 120 (d, C-5'), 126.9 (d, C-6'), 126.8 (d, C-7'), 125.1 (d, C-8'), 143.5 (s, C-8'a), 36.9 (t, C-9'); EIMS m/z 336 (100, M⁺), 335 (87), 334 (60), 307 (73), 306 (86), 304 (50), 292 (14), 171 (52), 152 (55), 143 (26), 115 (28).

Example 1m 1-(9'-Ethyl-3'-carbazole)-1,2,3,4-tetrahydro-β-carboline (16)

Yellow solid; $C_{25}H_{23}N_3$; IR (KBr) ν max 3470, 2930, 1465, 1390, 750 cm⁻¹; ¹H-NMR (CDCl₃) δ 6.04 (1H, s, H-1), 3.56 (1H, m, H-3a), 3.66 (1H, m, H-3b), 3.18 (1H, m, H-4a), 3.28 (1H, m, H-4b); $^{13}$C-NMR (CDCl$_3$) δ 59.2 (d, C-1), 42.3 (t, C-3), 19.8 (t, C-4), 110.2 (s, C-4a), 127.5 (s, C-4b), 121.7 (d, C-5), 119.4 (d, C-6), 118.3 (d, C-7), 110.9 (d, C-8), 143.9 (s, C-8a), 134.8 (s, C-9a), 125.1 (s, C-1'), 135.9 (s, C-2'), 125.1 (d, C-3'), 120.0 (d, C-4'), 141.2 (s, C-4'a), 141.8 (s, C-4'b), 120 (d, C-5'), 126.9 (d, C-6'), 126.8 (d, C-7'), 125.1 (d, C-8'), 143.5 (s, C-8'a), 36.9 (t, C-9'); EIMS m/z 365 (100, M$^+$), 364 (8), 336 (46), 335 (45), 319 (8), 306 (18), 223 (5.7), 208 (7.3),183 (18), 171 (39), 160 (51), 153 (18), 144 (15), 130 (5), 115 (11).

Example 1n 1-(4'-Chlorophenyl)-1,2,3,4-tetrahydro-β-carboline (17)

$^1$H-NMR (CDCl$_3$) δ 4.06 (2H, t, J=8.3 Hz, H-3), 2.99 (2H, t, J=8.3 Hz, H-4), 7.39 (1H, d, J=7.7 Hz, H-5), 7.32 (1H, dd, J=7.7, 7.2 Hz, H-6), 7.20 (1H, dd, J=7.8, 7.1 Hz, H-7), 7.67 (1H, d J=7.8 Hz, H-8), 8.04 (1H, s, NH-9), 7.49 (2H, d, J=8.6 Hz, H-2',6'), 7.71 (2H, d, J=8.6 Hz, H-3',5').

Example 1o 1-(4'-Bromophenyl)-1,2,3,4-tetrahydro-β-carboline (18)

C$_{17}$H$_{13}$N$_2$Br; $^1$H-NMR (CDCl$_3$) δ 4.05 (2H, t, J=7.6 Hz, H-3), 2.98 (2H, t, J=7.6 Hz, H-4), 7.39 (1H, d, J=8.0 Hz, H-5), 7.31 (1H, d, J=8.0 Hz, H-6), 7.20 (1H, t, J=7.2 Hz, H-7), 7.60 (1H, d, J=7.2 Hz, H-8), 8.00(1H, s, NH-9), 7.47 (4H, s, H-2',3',5',6').

Example 1p 1-(4'-Dimethylaminophenyl)-3,4-dihydro-β-carboline (20)

$^1$H-NMR (CD$_3$OD) δ 3.94 (2H, t, J=7.8 Hz, H-3), 3.31 (2H, overlap, H-4), 7.55 (1H, d, J=8.4 Hz, H-5), 7.21 (1H, t, J=7.5 Hz, H-6), 7.40 (1H, t, J=7.5 Hz, H-7), 7.75 (1H, d, J=8.1 Hz, H-8), 7.81 (2H, d, J=9.0 Hz, H-2',6'), 6.94 (2H, d, J=9.0 Hz, H-3',5'), 3.16 (6H, s, NMe$_2$).

Example 1q 1-(4'-Diethylaminophenyl)-3,4-dihydro-β-carboline (21)

$^1$H-NMR (CDCl$_3$) δ 3.08 (2H, dd, J=7.8, 15.3 Hz, H-3), 3.09 (2H, t, J=7.2 Hz, 1H-4), 7.62 (1H, d, J=8.4 Hz, H-5), 7.20 (1H, t, J=7.8 Hz, H-6), 7.38 (1H, t, J=7.8 Hz, 1H-7), 7.68 (1H, d, J=7.8 Hz, H-8), 10.6 (1H, brs, NH-9), 7.94 (2H, d, J=9.0 Hz, H-2',6'), 6.55 (2H, d, J=9.0 Hz, H-3',5'), 1.08 (6H, t, J=6.9 Hz, CH2<u>CH$_3$</u>), 3.23 (4H, q, J=6.9 Hz, <u>CH$_2$</u>CH$_3$).

Example 1r 1-(2',4'-Dimethoxyphenyl)-3,4-dihydro-β-carboline (22)

$^1$H-NMR (CDCl$_3$) δ 4.07 (2H, t, J=8.4 Hz, H-3), 3.10 (2H, t, J=8.4 Hz, H-4), 7.54 (1H, d, J=8.4 Hz, H-5), 7.41 (1H, d, J=8.4 Hz, H-6), 7.34 (1H, t, J=8.4 Hz, H-7), 7.63 (1H, d, J=8.4 Hz, H-8), 6.53 (1H, d, J=1.8 Hz, H-3'), 6.57 (1H, d, J=7.2, 1.8 Hz, H-5'), 7.19 (1H, d, J=7.2 Hz, H-6'), 3.82, 3.84 (6H, s, OMe).

Example 1s 1-(3',4'-Dimethoxyphenyl)-3,4-dihydro-β-carboline (23)

$^1$H-NMR (CDCl$_3$) δ 3.98 (2H, t, J=7.8 Hz, H-3), 2.96 (2H, t, J=7.8 Hz, H-4), 7.40 (1H, d, J=8.4 Hz, H-5), 7.20 (1H, d, J=8.4 Hz, H-6), 7.66 (1H, d, J=8.4 Hz, H-8), 7.30 (1H, d, J=1.8 Hz, H-2'), 6.86 (1H, d, J=7.8 Hz, H-5'), 7.15 (1H, d, J=7.8 Hz, H-6'), 3.77, 3.82, 3.84 (6H, s, OMe).

Example 1t 1-(2',5'-Dimethoxyphenyl)-3,4-dihydro-β-carboline (24)

$^1$H-NMR (CDCl$_3$) δ 4.11 (2H, t, J=8.6 Hz, H-3), 2.99 (2H, t, J=8.6 Hz, H-4), 7.34 (1H, d, J=8.1 Hz, H-5), 7.27 (1H, d, J=7.4 Hz, H-6), 7.15 (1H, t, J=7.4 Hz, H-7), 7.63 (1H, d, J=8.1 Hz, H-8), 8.50 (1H, brs, H-9), 7.00 (2H, s, H-3',4'), 7.06 (1H, s, H-6'), 3.81 (6H, s, OMe).

Example 1u 1-(3',5'-Dimethoxyphenyl)-3,4-dihydro-β-carboline (25)

$^1$H-NMR (CDCl$_3$) δ 4.05 (2H, t, J=8.4 Hz, H-3), 2.98 (2H, t, J=8.4 Hz, H-4), 7.37 (1H, d, J=8.1 Hz, H-5), 7.18 (1H, t, J=7.5 Hz, H-6), 7.31 (1H, t, J=7.5 Hz, H-7), 7.66 (1H, d, J=8.1 Hz, H-8), 8.38)1H, s, H-9), 6.88 (2H, d, J=2.1 Hz, H-2',6'), 6.58 (1H, dd, J=2.4, 2.1 Hz, H-4'), 3.83 (6H, s, OMe).

Example 1v 1-(3',4',5'-Trimethoxyphenyl)-3,4-dihydro-β-carboline (26)

$^1$H-NMR (CDCl$_3$) δ 4.06 (2H, dd, J=8.1, 16.5 Hz, H-3), 3.01 (2H, dd, J=8.1, 16.5 Hz, H-4), 7.43 (1H, d, J=8.1 Hz, H-5), 7.22 (1H, dd, J=8.1, 7.8 Hz, H-6), 7.36 (1H, t, J=7.8 Hz, H-7), 7.69 (1H, d, J=7.8 Hz, H-8), 8.28 (1H, brs, H-9), 6.99 (2H, s, H-2',6'), 3.92 (6H, s, OMe).

Example 1w:

1-(3'-Nitro-4'-Benzo-1",3"-dioxole)-3,4-dihydro-β-carboline (27)

$^1$H-NMR (CDCl$_3$)δ4.08 (2H, t, J=8.6 Hz, H-3), 3.06 (2H, t, J=8.6 Hz, H-4), 7.30 (1H, overlap, H-5), 7.20 (2H, overlap, H-6,7), 7.65 (1H, d, J=7.8 Hz, H-8), 8.11(1H, s, H-9), 6.94 (1H, s, H-2'), 7.63 (1H, s, H-5'), 6.19 (2H, s, OCH$_2$O).

Example 1x 1-(2'-Fluorenyl)-3,4-dihydro-β-carboline (28)

$^1$H-NMR (CDCl$_3$) δ 3.03 (2H, t, J=7.8 Hz, H-3), 4.09 (2H, t, J=7.8 Hz, H-4), 3.99 (2H, s, H-9'), 7.20 (1H, t), 7.35 (1H, t), 7.40 (3–4H, m), 7.58 (1H, d), 7.66 (1H, d, J=7.8 Hz), 7.80 (1H, d), 7.83 (1H, d), 7.88 (1H, d, J=7.8 Hz), 8.00 (1H, s).

Example 1y 1-(9'-Ethyl-3'-carbazole)-3,4-dihydro-β-carboline (29)

$^1$H-NMR (CDCl$_3$) δ 3.01 (2H, m, H-3), 2.60 (2H, m, H-4), 1.41 (3H, t, J=7.2 Hz, CH$_2$<u>CH$_3$</u>), 4.32 (2H, q, J=7.2 Hz, <u>CH$_2$</u>CH$_3$), 7.0–7.6 (m), 8.00 (1H, d), 8.11 (1H, s).

Example 2

Table 1 shows the IC$_{50}$ values for compounds 4–29, pacitaxel (taxol), and manzamine A (3) as tested against murine P-388 (leukemia) and human tumor cells including KB-16 (nasopharyngeal carcinoma), A-549 (lung adenocarcinoma), and HT-29 (colon adenocarcinoma) in vivo.

TABLE 1

Biological Evaluation of 1-Substituted 1,2,3,4-Tetrahydro-β-Carboline and 3,4-Dihydro-β-Carbolines.

| Compound | R | P-388 A | P-388 B | KB-16 A | KB-16 B | A-549 A | A-549 B | HT-29 A | HT-29 B |
|---|---|---|---|---|---|---|---|---|---|
| 4 | 4'-Cl-phenyl (1') | 0.2 | | 0.7 | | 0.6 | | 0.9 | |
| 17 | | | 0.5 | | 0.9 | | 1.2 | | 1.3 |
| 5 | 4-Br-phenyl | 1.0 | | 2.1 | | 3.0 | | 1.1 | |
| 18 | | | 1.1 | | 2.4 | | 3.0 | | 1.2 |
| 6 | 4-NO₂-phenyl | 0.8 | | 1.1 | | 0.9 | | 1.5 | |
| 7 | 4-N(Me)₂-phenyl | 2.2 | | 1.7 | | 1.6 | | 0.7 | |
| 20 | | | 2.9 | | 4.8 | | 50 | | 3.0 |
| 8 | 4-N(Et)₂-phenyl | 0.07 | | 0.2 | | 1.1 | | 1.1 | |
| 21 | | | 0.7 | | 0.3 | | 1.8 | | 1.3 |
| 9 | 2-MeO, 4-OMe-phenyl | 0.6 | | 0.7 | | 1.1 | | 1.1 | |
| 22 | | | 0.6 | | 2.7 | | 0.5 | | 0.5 |
| 10 | 2-OMe, 4-OMe-phenyl | 2.8 | | >50 | | >50 | | >50 | |
| 23 | | | 2.7 | | 15 | | 12 | | 2.7 |
| 11 | 2-OMe, 5-MeO-phenyl | 2.6 | | 3.7 | | 2.0 | | 2.2 | |
| 24 | | | 1.1 | | 0.7 | | 0.2 | | 0.4 |
| 12 | | 0.2 | | 1.4 | | 0.6 | | 0.4 | |

TABLE 1-continued

Biological Evaluation of 1-Substituted 1,2,3,4-Tetrahydro-β-Carboline and 3,4-Dihydro-β-Carbolines.

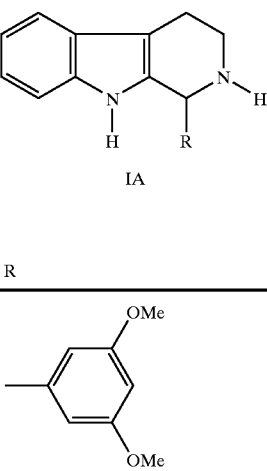
IA

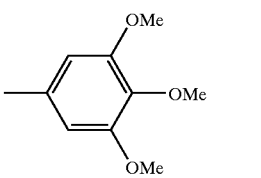
IB

| Compound | R | P-388 A | P-388 B | KB-16 A | KB-16 B | A-549 A | A-549 B | HT-29 A | HT-29 B |
|---|---|---|---|---|---|---|---|---|---|
| 25 | 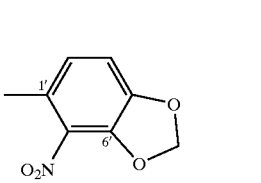 | | 0.4 | | 1.0 | | 0.6 | | 0.6 |
| 13 |  | 1.2 | | 8.3 | | 2.0 | | 1.6 | |
| 26 | | | 1.2 | | 1.4 | | 0.5 | | 0.7 |
| 14 | 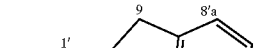 | 0.3 | | 6.0 | | 1.7 | | 1.4 | |
| 27 | | | 0.3 | | 0.8 | | 0.6 | | 1.0 |
| 15 | 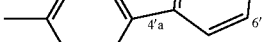 | 0.1 | | 0.4 | | 0.6 | | 0.5 | |
| 28 | | | 0.1 | | 1.4 | | 0.6 | | 0.7 |
| 16 |  | 0.7 | | 0.8 | | 0.8 | | 0.5 | |
| 29 | | | <0.001 | | <0.001 | | <0.001 | | <0.001 |
| 30 | (paclitaxel) | <0.001 | | <0.001 | | <0.001 | | <0.001 | |
| 3 | (manzamine A) | 0.07 | | <0.001 | | 0.03 | | 0.1 | |

The concentration (μg/ml) of compound inhibiting 50% (IC$_{50}$) of the growth of tumor cell lines, P-388 (murine leukemia), KB-16 (human nasopharyngeal carcinoma), A-549 (human lung adenocarcinoma), and HT-29 (human colon adenocarcinoma), after 3, 3, 6, and 6 day drug exposure.

Example 3

Compound (29) was shown in Example 2 to exhibit potent activity against the tested cell lines. Accordingly, compound (29) was screened in the HepG2/A2, HeLa, H1299, SCM-1, and normal skin fibroblast cell lines.

HepG2/A2 is a human hepatocellular carcinoma cell line, and it carries hepatitis B virus (HBV) intact genome and secretes HBV surface antigen (HbsAg). The cell growth is serum-independent so HepG2/A2 has been used as model system for screening anti-HBV and anticancer drugs.

Hep G2/A2 cells were treated with various concentrations of (29) for 2, 4 and 6 days. Cells were harvested and viable cells were determined by trypan blue exclusion, and cells were counted with hemocytometer. Data are expressed as mean±S.D. (n=3).

The results are depicted in FIG. 1.

Figure 2:
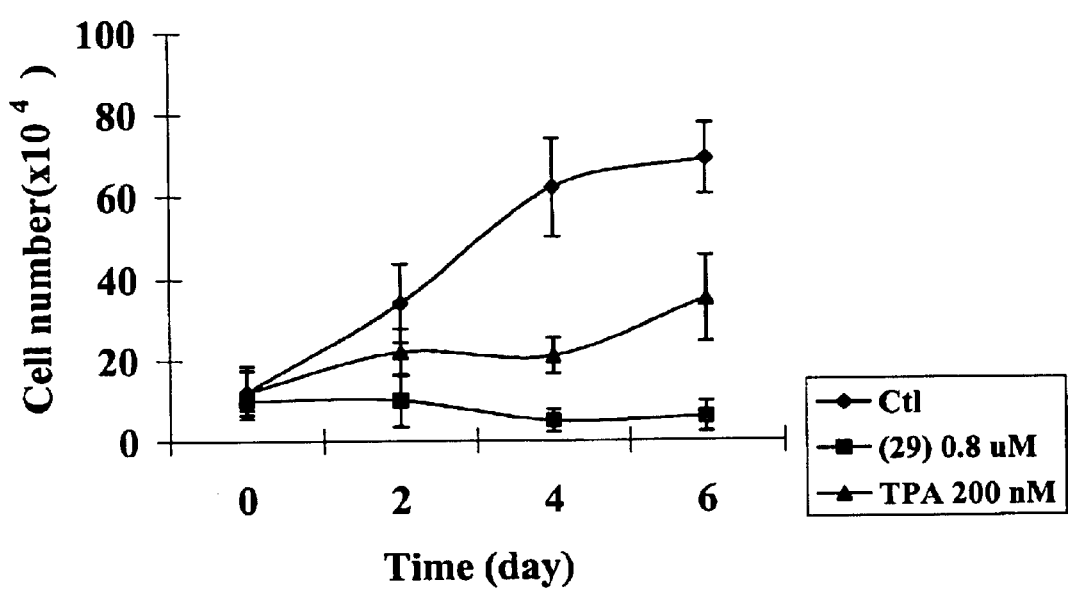
FIG. 2 graphically depicts the growth inhibition effects of 0.825 μM (29) or 200 nM TPA (12-O-tetradecanoyl-phorbol-13-acetate) in serum free medium for 2, 4, and 6 days.

Hep G2/A2 cells were cultured in the absence or presence of 200 nM TPA (12-0-tetradecnoyl-phorbol-13-acetate, a tumour promoter) or 0.825 $\mu$M (29) in serum-free medium for 2, 4 and 6 days. Viable cells were determined by trypan blue exclusion and cells were counted in a hemocytometer. Data are expressed as mean±S.D. (n=3). The results are depicted in FIG. 2.

Figure 3:
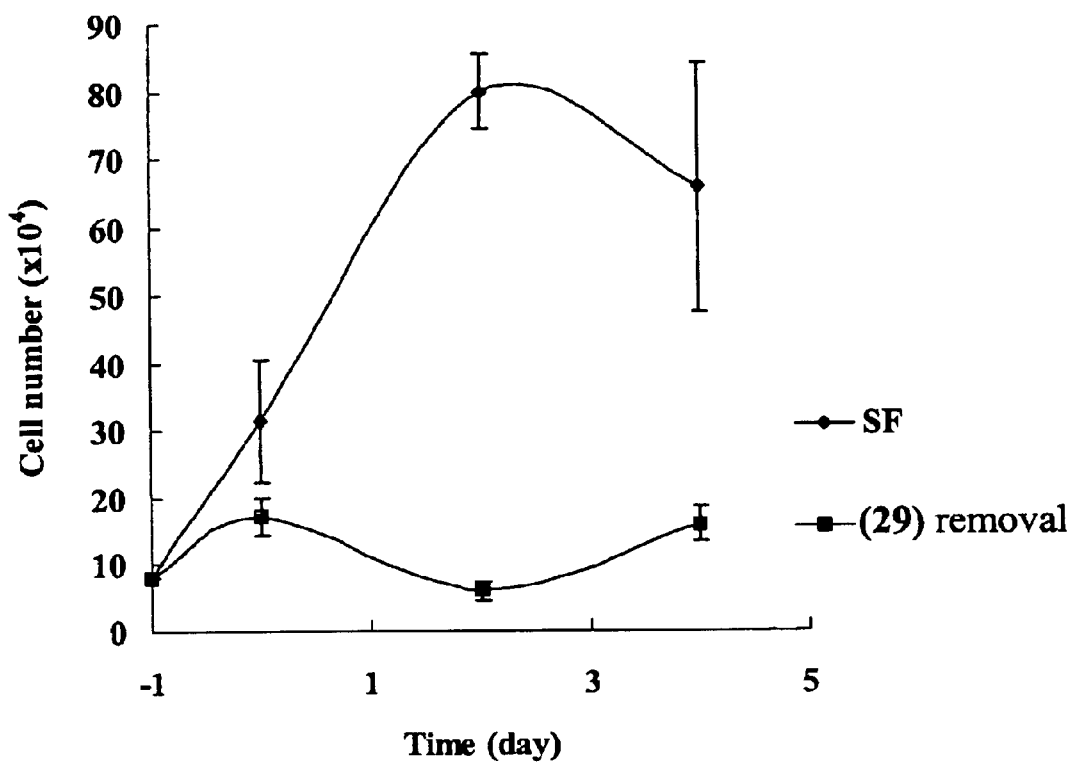
FIG. 3 graphically depicts the growth of HepG2/A2 cells cultured in the absence or presence of 0.8 μM (29) in serum free medium for 24 hours, followed by changing to fresh medium and incubating for another 4 days.

Hep G2/A2 cells were cultured in the absence or presence of 0.8 $\mu$M (29) in serum free medium for 24 hr. The cells were then changed to a fresh medium without (29) and incubated for another 4 days. Viable cells were determined by trypan blue exclusion, and cells were counted with a hemocytometer every two days. Data are expressed as mean ±S.D. (n=3). The results are depicted in FIG. 3.

Log phase growth cultures of Hep G2/A2 cells were treated with or without 0.8 $\mu$M (29) in serum-free medium for 24, 48, 72 hr. After treatment, cells were fixed, and stained with propidium iodide. Their DNA contents were analysed using FACScan. The results are depicted in FIG. 4.

Log phase growth cultures of HeLa cells were treated with or without 4 $\mu$M (29) for 4, 8, 12, and 16, hrs. After treatment, cells were fixed, and stained with propidium iodide. Their DNA contents were analysed using FACSean. The results are depicted in FIG. 5.

HeLa were cells were synchronized at G1/S boundary by treating cells with 2 mM hydroxyurea for 14–16 hr. After release, cells were incubated in 4 $\mu$M (29) containing medium or drug-free medium for 4, 8, 12, and 16 hr. After treatment, cells were fixed, and stained with propidium iodide. Their DNA contents were analyzed using FACScan.

The results are depicted in FIG. 6.

HeLa cells were synchronized at M phase by treating cells with 0.7 $\mu$M nocodazole for 16 hr. After release, cells were incubated in 4 $\mu$M (29) containing medium or drug free medium for 4, 8, 12, 16 hr. After treatment, cells were fixed, and stained with 10 propidium iodide. Their DNA contents were analysed using FACScan.

The results are depicted in FIG. 7.

Figure 8:
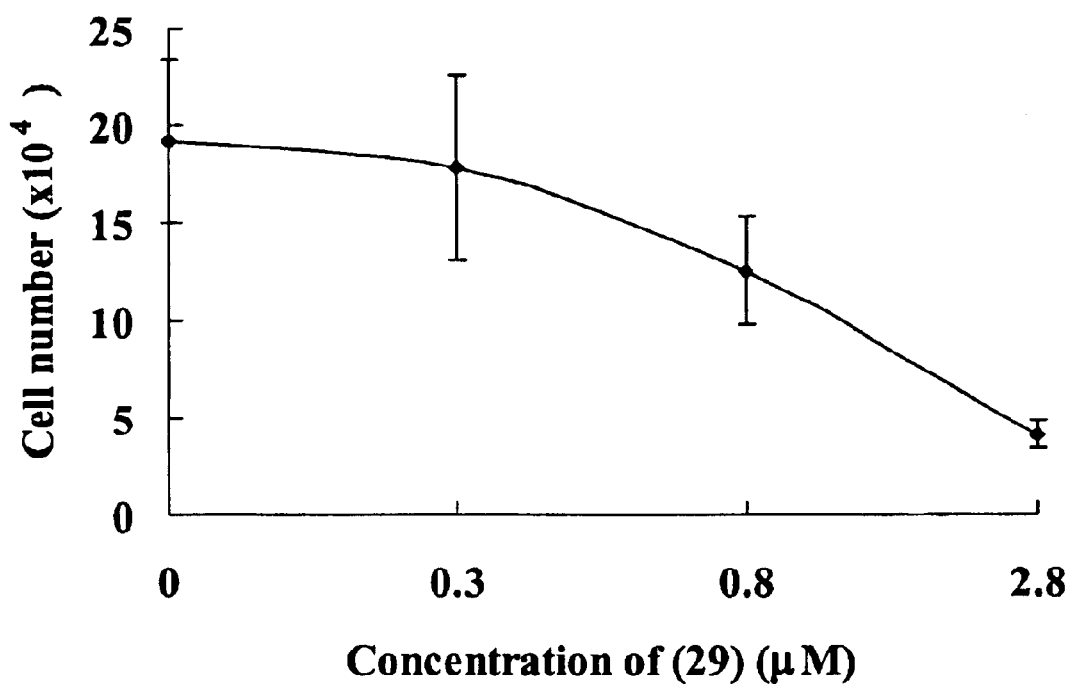
FIG. 8 depicts the effect of (29) on SCM-1 cells.

SCM-1 cells (stomach carcinoma cell line) were seeded on 24-wells plate at $5 \times 10^5$ cells/well. After 24 hr, medium were changed to fresh DMEM containing 10% serum and treated with various concentrations of (29) for 2 days. Viable cells were determined by trypan blue exclusion, and cells were counted in hemocytometer. Data are expressed as mean±SEM (n=3). The results are depicted in FIG. 8.

Figure 9:
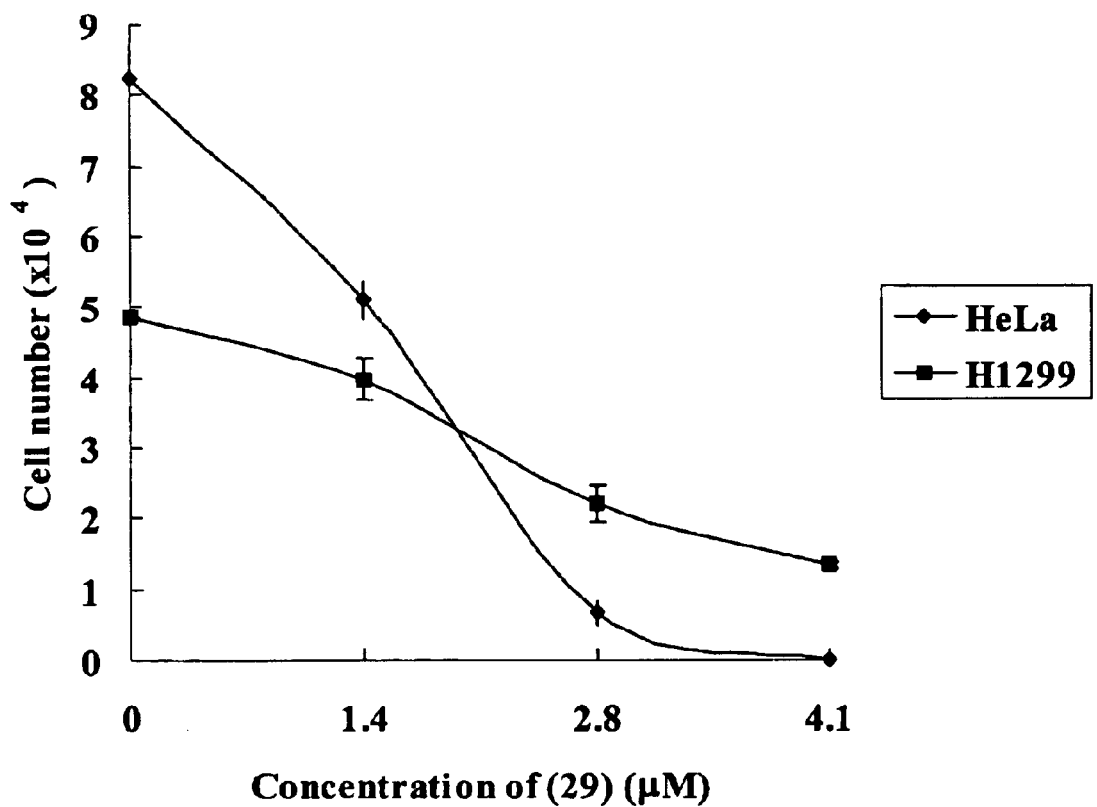
FIG. 9 graphically depicts the effects of (29) on HeLa and H1299 cell lines.

HeLa cells were seeded on 24-wells plate at $2 \times 10^5$ cells/well. After 24 hr, medium were changed to fresh DMEM containing 10% serum and treated with various concentrations of (29) for 2 days. Viable cells were determined by trypan blue exclusion, and cells were counted in hemocytometer. Data are expressed as mean±SEM (n—3). In H1299 cells (small cell lung cancer cell line), cells were incubated with RPMI containing 10% serum. The results are depicted in FIG. 9.

Example 4

The growth effects of compound 29 was tested on 8 different human tumour cell lines. Changes in cell proliferation based on the ability of viable cells to cause alamar Blue to change from its oxidized (non-fluorescent, blue) to a reduced (fluorescent, red) form were evaluated. With the results obtained from the alamarBlue reaction, cell proliferation was quantified and metabolic activity of viable cells examined. Test compound, (29), was tested for its effect on the proliferation of 8 different human tumor cell lines at five final assay concentrations from 100 to 0.01 $\mu$M through serial 10-fold dilutions, respectively.

Test Substance and Concentration

Compound 29 was dissolved in 100% ethanol and then diluted with Phosphate Buffer Saline (PBS, pH=7.4) to obtain initial working solutions of 10000, 1000, 100, 10 and 1 $\mu$M in 40% ethanol. In testing, 100-fold dilution was made in culture media to get final assay concentrations of 100, 10, 1, 0.1 and 0.01 $\mu$M in 0.4% of ethanol.

| Cell Culture Media | |
|---|---|
| Cell Lines | Culture Medium |
| T47D | RPMI 1640, 80%; Fetal Bovine Serum, 20%, supplemented with 0.2 I.U. bovine insulin per ml |
| PC-6, U937 | RPMI 1640, 90%; Fetal Bovine Serum, 10% |
| PC-3 | F-12 Nutrient Mixture (Ham), 90%: Fetal Bovine Serum, 10% |
| MCF-7, Hep G2 | Minimum Essential Medium, 90%; Fetal Bovine Serum, 10% |
| HT-29 | McCoy's Medium, 90%; Fetal Bovine Senim, 10% |
| HL-60 | RPMI 1640, 80%; Fetal Bovine Serum, 20% |

All of media were supplemented with 1% Antibiotic-Antimycotic.

| Cell Lines | | |
|---|---|---|
| Cell Name | Source | Type of Cell Line |
| MCF-7 | ATCC HTB-22 | Breast adenocarcinoma. Pleural effusion, human. |
| T47D | ATCC HTB-133 | Breast, ductal carcinoma, pleural effusion, human. |
| HT-29 | ATCC HTB-38 | Colon, adenocarcinoma, moderately well-differentiated grade II, human. |
| HL-60 | ATCC CCL-240 | Promyelocytic leukemia, human. |
| HepG2 | ATCC HB-8065 | Hepatoblastoma, liver, human. |
| PC-6 | Hokkaido Univ., Japan | Lung, carcinoma, human. |
| U-937 | ATCC CRL-1593 | Histiocytic lymphoma, human. |
| PC-3 | ATCC CRL-1435 | Prostate, adenocarcinoma, human. |

All of the human tumor cell lines were obtained from American Type Culture Collection (ATCC) except PC-6 (lung) from Hokkaido University, Japan and the tumor cells were all incubated at 37° C. with 5% $CO_2$ in air atmosphere.

Chemicals

Minimum Essential medium (GIBCO BRL, U.S.A.), Fetal Bovine Serum (GIBCO BRL, U.S.A.), Antibiotics-Antimycotic (GIBCO BRL, U.S.A.), McCoy's Medium (G1)3C0 BRL, U.S.A.), F-12 Nutrient Mixture (Ham) (GIBCO BRL, U.S.A.), RPMI 1640 (HyClone, U.S.A.), Mitomycin (Sigma, U.S.A.), Dimethylsulfoxide (Merck, Germany) and AlamarBlue (Biosource, U.S.A.).

Equipment $CO_2$ Incubator (Forma Scientific Inc., U.S.A.), Inverted Microscope CK-4015 (Olympus, Japan), System Microscope BX-40 (Olympus, Japan), Centrifuge CT6D (Hitachi, Japan), Vertical Laminar Flow (High-Ten, Taiwan), Hemacytometer (Hausser Scientific Horsham, U.S.A.) and Spectrafluor Plus (Tecan, Austria).

Evaluation of Anti-Proliferation for Test Substance

Aliquots of 100 µl of cell suspension (about 2.5–5×10³/well) were placed in 96well microtiter plates in an atmosphere of 5% $CO_2$ at 37° C. After 24 hours, 100 µl of growth medium, 2 µL of test solution or vehicle (40% DMSO), was added respectively per well in duplicate for an additional 72 hour incubation. Thus, the final concentration of DMSO was 0.4%. The test compound was evaluated at concentrations of 100, 10, 1, 0.1 and 0.01 µM. At the end of the incubation, 20 µL of alamarBlue 75% reagent was added to each well for another 6-hour incubation before detection of cell viability by fluorescent intensity. Fluorescent intensity was measured using a Spectrafluor Plus plate reader with excitation at 530 nm and emission at 590 nm.

Determination of $IC_{50}$, TGI and $LC_{50}$

The measured results were calculated according to the following formula:

cytostatic or cytotoxic activity, and a semi-quantitative $IC_{50}$, TGI and $LC_{50}$ were then determined by nonlinear regression using GraphPad Prism (GraphPad Software, U.S.A.).

$IC_{50}$ (50% Inhibition Concentration): Test Compound concentration at which the increase from $time_0$ in the number or mass of treated cells was only 50% as much as the corresponding increase in the vehicle-control at the end of experiment.

TGI (Total Growth Inhibition): Test compound concentration at which the number or mass of treated cells at the end of the experiment was equal to that at $time_0$.

$LC_{50}$ (50% Lethal Concentration): Test compound concentration at which the number of mass of treated cells at the end of the experiment was half that at $time_0$.

TABLE 1-1

The Percent Growth in Variable Concentrations of Test Compound (29) for Human Tumor Cells

| | | | | Percent Growth (Mean ± SEM, n = 2) | | | | |
|---|---|---|---|---|---|---|---|---|
| Assay | | | | Concentration (µM) | | | | |
| Name | Blank | $Time_0$ | Vehicle | 100 | 10 | 1 | 0.1 | 0.01 |
| Breast MCF-7 | −100 | 0 | 100 | −100 ± 0 | −48 ± 11 | 85 ± 8 | 94 ± 7 | 97 ± 1 |
| Breast T47D | −100 | 0 | 100 | −100 ± 4 | 25 ± 3 | 89 ± 3 | 88 ± 6 | 92 ± 2 |
| Colon HT-29 | −100 | 0 | 100 | −94 ± 3 | −30 ± 15 | 85 ± 3 | 101 ± 8 | 97 ± 4 |
| Leukemia HL-60 | −100 | 0 | 100 | −100 ± 2 | 9 ± 3 | 73 ± 5 | 90 ± 6 | 99 ± 2 |
| Liver HepG2 | −100 | 0 | 100 | −100 ± 3 | −27 ± 7 | 81 ± 4 | 96 ± 11 | 106 ± 2 |
| Lung PC-6 | −100 | 0 | 100 | −79 ± 11 | 24 ± 2 | 95 ± 5 | 97 ± 5 | 101 ± 1 |
| Lymphoma U-937 | −100 | 0 | 100 | −93 ± 0 | −3 ± 4 | 90 ± 2 | 97 ± 6 | 103 ± 3 |
| Prostate PC-3 | −100 | 0 | 100 | −93 ± 1 | −17 ± 9 | 82 ± 4 | 94 ± 3 | 100 ± 1 |

A decrease of 50% or more (>50%) in fluorescence intensity relative to the vehicle-treated control indicated significant growth inhibition, cytostatic or cytotoxic activity.

$PG(\%) = 100 \times (\text{Mean } F_{test} - \text{Mean } F_{time0}) / (\text{Mean } F_{ctrl} - \text{Mean } F_{time0})$.

If (Mean $F_{test}$ − Mean $F_{time0}$) < 0, then $PG(\%) = 100 \times (\text{Mean } F_{test} - \text{Mean } F_{time0}) / (\text{Mean } F_{time0} - \text{Mean } F_{blank})$ Where PG stands for percent growth.

Mean $F_{time0}$ = The average of 2 measured fluorescent intensities of reduced alamarBlue at the time just before exposure of cells to the test substance.

Mean $F_{test}$ = The average of 2 measured fluorescent intensities of alamarBlue after 72-hour exposure of cells to the test substance.

Mean $F_{ctrl}$ = The average of 2 measured fluorescent intensities of alamarBlue after 72-hour incubation without the test substance.

Mean $F_{blank}$ = The average of 2 measured fluorescent intensities of alamarblue in medium without cells after 72-hour incubations.

A decrease of 50% or more (≧50%) in fluorescent intensity relative to vehicle-treated control indicated significant

TABLE 2-1

The Estimated $IC_{50}$, TGI and $LC_{50}$

| Test Compound | Assay Name | [a]$IC_{50}$ | [b]TGI | [c]$IC_{50}$ |
|---|---|---|---|---|
| 29 | Breast, MCF-7 | 2.0 µM | 4.2 µM | 8.3 µM |
| 29 | Breast, T47D | 6.0 µM | 10.8 µM | 19.2 µM |
| 29 | Colon, HT-29 | 2.3 µM | 5.2 µM | 11.7 µM |
| 29 | Leukemia, HL-60 | 3.2 µM | 8.3 µM | 22.0 µM |
| 29 | Liver, HepG2 | 2.2 µM | 5.2 µM | 12.5 µM |
| 29 | Lung, PC-6 | 5.0 µM | 12.5 µM | 32.5 µM |
| 29 | Lymphoma, U-937 | 3.5 µM | 7.9 µM | 18.3 µM |
| 29 | Prostate, PC-3 | 2.5 µM | 6.2 µM | 15.0 µM |

[a]$IC_{50}$ (50% Inhibition Concentration): Test compound concentration where the increase from $time_0$ in the number or mass of treated cells was only 50% as much as the corresponding increase in the vehicle-control at the end of experiment.
[b]TGI (Total Growth Inhibition): Test compound concentration where the number or mass of treated cells at the end of the experiment was equal to that at $time_0$.
[c]LC50 (50% Lethal Concentration): Test compound concentration where the number or mass of treated cells at the end of experiment was half that at $time_0$.

While the invention has been described with respect to a limited number of examples, those skilled in the art, having benefit of this disclosure, will appreciate that other embodiments can be devised without departing from the scope of the invention as disclosed herein. Accordingly, the scope of the invention should be limited only by the attached claims.

What is claimed is:

1. A method for inhibiting cancer cell proliferation, comprising administering an effective amount of a compound according to formula (II) or (III) to a subject in need thereof,

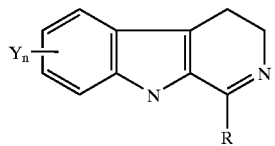

(II)

wherein Y is a substituent selected from the group consisting of hydroxy, $C_{1-6}$ alkoxy, benzyloxy, $C_{1-6}$ acyloxy, amino, $C_{1-6}$ alkyl, $C_{1-6}$ dialkylamino, halogen, and carboxy, and n is 0, 1, 2, 3, or 4, and R is

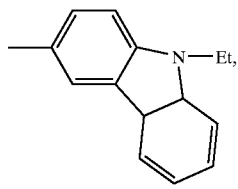

and wherein the cancer cell is one selected from breast cancer cell, colon cancer cell, leukaemia cancer cell, liver cancer cell, lung cancer cell, lymphoma, and prostate cancer cell.

2. The method of claim 1, wherein the compound is in a composition comprising at least one selected from the group consisting of a pharmaceutically acceptable carrier, a pharmaceutically acceptable diluent, and a pharmaceutically acceptable excipient.

3. A composition comprising a compound according to formula (II) or(III), or a salt or a prodrug thereof,

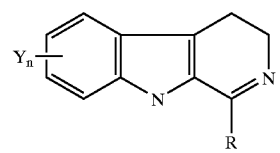

(II)

wherein Y is a substituent selected from the group consisting of hydroxy, $C_{1-6}$ alkoxy, benzyloxy, $C_{1-6}$ acyloxy, amino, $C_{1-6}$ alkyl, $C_{1-6}$ dialkylamino, halogen, and carboxy, and n is 0, and R is

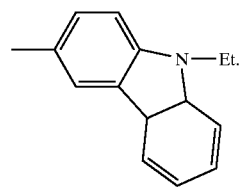

4. The composition of claim 3, further comprising at least one selected from the group consisting of a pharmaceutically acceptable carrier, a pharmaceutically acceptable diluent, and a pharmaceutically acceptable excipient.

5. The composition of claim 3, wherein the compound is in a form of the salt or the prodrug.

6. The composition of claim 5, further comprising at least one selected from the group consisting of a pharmaceutically acceptable carrier, a pharmaceutically acceptable diluent, and a pharmaceutically acceptable excipient.

* * * * *